(12) United States Patent
Errico et al.

(10) Patent No.: US 9,211,182 B2
(45) Date of Patent: Dec. 15, 2015

(54) ANTI-REFLUX DEVICES AND METHODS FOR TREATING GASTRO-ESOPHAGEAL REFLUX DISEASE (GERD)

(71) Applicant: E2, LLC, Short Hills, NJ (US)

(72) Inventors: Joseph P. Errico, Warren, NJ (US); John T. Raffle, Austin, TX (US); Michael W. Dudasik, Nutley, NJ (US)

(73) Assignee: E2, LLC, Short Hills, NJ (US)

( * ) Notice: Subject to any disclaimer, the term of this patent is extended or adjusted under 35 U.S.C. 154(b) by 288 days.

(21) Appl. No.: 13/862,443

(22) Filed: Apr. 14, 2013

(65) Prior Publication Data
US 2013/0304231 A1 Nov. 14, 2013

Related U.S. Application Data

(62) Division of application No. 12/900,569, filed on Nov. 20, 2009, now abandoned.

(51) Int. Cl.
*A61F 2/04* (2013.01)
*A61M 5/00* (2006.01)
*A61F 5/00* (2006.01)

(52) U.S. Cl.
CPC ............... *A61F 2/04* (2013.01); *A61F 5/0079* (2013.01); *A61F 2002/044* (2013.01); *A61F 2230/0006* (2013.01); *A61F 2230/0065* (2013.01); *A61F 2230/0067* (2013.01); *A61F 2250/0003* (2013.01); *A61F 2250/0013* (2013.01)

(58) Field of Classification Search
CPC ... A61F 2/04; A61F 2002/044; A61F 5/0076; A61F 5/0079; A61F 2002/045
See application file for complete search history.

(56) References Cited

U.S. PATENT DOCUMENTS

| | | |
|---|---|---|
| 3,159,176 A | 12/1964 | Russell et al. |
| 4,265,694 A | 5/1981 | Boretos et al. |
| 4,271,827 A | 6/1981 | Angelchik |
| 4,434,810 A | 3/1984 | Atkinson |
| 4,846,836 A | 7/1989 | Reich |
| 5,314,473 A | 5/1994 | Godin |

(Continued)

FOREIGN PATENT DOCUMENTS

| | | | |
|---|---|---|---|
| CA | 2461658 | * 10/2003 | ............. A61M 3/00 |
| WO | 2005/032422 A2 | 4/2005 | |
| WO | 2007/137026 A2 | 11/2007 | |

OTHER PUBLICATIONS

J AW Bingham. "Evolution and early results of constructing an anti-reflux valve in the stomach". Proc. Roy. Soc. Med. 67 (1974):4-8.

(Continued)

*Primary Examiner* — Andrew Iwamaye
(74) *Attorney, Agent, or Firm* — Dentons US LLP

(57) ABSTRACT

Devices, systems, and methods for treating gastro-esophageal reflux disease (GERD) include anti-reflux valves and retainers for securing them within the lumen of the esophagus, stomach, or a hiatal hernia. The retainers contain inflatable balloons, some of which may be enveloped by a flexible shell that is used to secure the balloon to tissue. Methods are described for treating GERD patients who (1) have no hiatal hernia, (2) have a hiatal hernia that is fixed in place, or (3) have a hiatal hernia that slides above and below the diaphragm. Methods are also described for delivering GERD-treatment devices to their target locations within the patient's gastrointestinal tract.

9 Claims, 13 Drawing Sheets

(56) References Cited

U.S. PATENT DOCUMENTS

| | | | |
|---|---|---|---|
| 5,716,385 A | 2/1998 | Mittal et al. | |
| 5,861,036 A | 1/1999 | Godin | |
| 6,097,984 A | 8/2000 | Douglas | |
| 6,264,700 B1 | 7/2001 | Kilcoyne et al. | |
| 6,302,917 B1 | 10/2001 | Dua et al. | |
| 6,544,291 B2 | 4/2003 | Taylor | |
| 6,746,489 B2 | 6/2004 | Dua et al. | |
| 6,764,518 B2 | 7/2004 | Godin | |
| 6,790,237 B2 | 9/2004 | Stinson | |
| 6,887,215 B2 | 5/2005 | McWeeney | |
| 6,958,079 B1 | 10/2005 | Taylor et al. | |
| 7,118,600 B2 | 10/2006 | Dua et al. | |
| 7,146,216 B2 | 12/2006 | Bumm | |
| 7,354,455 B2 | 4/2008 | Stinson | |
| 7,402,197 B2 | 7/2008 | Larsen et al. | |
| 7,445,642 B2 | 11/2008 | Amos et al. | |
| 7,632,291 B2 | 12/2009 | Stephens et al. | |
| 2002/0032487 A1 | 3/2002 | Dua et al. | |
| 2002/0077696 A1 | 6/2002 | Zadno-Azizi et al. | |
| 2003/0060894 A1 | 3/2003 | Dua et al. | |
| 2003/0191525 A1 | 10/2003 | Thornton | |
| 2003/0212452 A1 | 11/2003 | Zadno-Azizi et al. | |
| 2004/0102855 A1 | 5/2004 | Shank | |
| 2004/0230297 A1 | 11/2004 | Thornton | |
| 2004/0243223 A1 | 12/2004 | Kraemer | |
| 2005/0065614 A1 | 3/2005 | Stinson | |
| 2006/0020332 A1* | 1/2006 | Lashinski et al. | 623/2.11 |
| 2006/0041319 A1 | 2/2006 | Taylor | |
| 2006/0058889 A1 | 3/2006 | Case et al. | |
| 2006/0064174 A1 | 3/2006 | Zadno | |
| 2006/0276812 A1 | 12/2006 | Hill et al. | |
| 2007/0016306 A1 | 1/2007 | Dua et al. | |
| 2007/0112437 A1 | 5/2007 | Shank | |
| 2007/0208429 A1 | 9/2007 | Leahy | |
| 2008/0133002 A1 | 6/2008 | Gelbart et al. | |
| 2008/0223476 A1 | 9/2008 | Stinson | |
| 2008/0228285 A1 | 9/2008 | Kraemer et al. | |
| 2009/0259093 A1 | 10/2009 | Bhat et al. | |
| 2009/0259315 A1 | 10/2009 | Banik | |
| 2010/0036504 A1 | 2/2010 | Sobrino-Serrano et al. | |
| 2010/0049221 A1 | 2/2010 | Baker et al. | |
| 2010/0076481 A1 | 3/2010 | Stephens et al. | |
| 2010/0076573 A1 | 3/2010 | Kugler et al. | |
| 2010/0087809 A1 | 4/2010 | Edwards et al. | |
| 2010/0114327 A1 | 5/2010 | Sobrino-Serrano | |
| 2010/0121461 A1 | 5/2010 | Sobrino-Serrano et al. | |
| 2010/0121462 A1 | 5/2010 | Sobrino-Serrano et al. | |
| 2010/0137891 A1 | 6/2010 | Shalon et al. | |
| 2010/0137998 A1 | 6/2010 | Sobrino-Serrano et al. | |
| 2011/0004320 A1* | 1/2011 | Priplata et al. | 623/23.65 |
| 2012/0016468 A1* | 1/2012 | Robin et al. | 623/2.11 |
| 2012/0095483 A1* | 4/2012 | Babkes et al. | 606/153 |

OTHER PUBLICATIONS

D. Chen, et al. "Systematic review of endoscopic treatments for gastro-oesophageal reflux disease". British Journal of Surgery 2009; 96: 128-136.

Derick J. Christian, et al. "Current Status of Antireflux Surgery". Surg Clin N Am 85 (2005) 931-947.

Filipi J. Christian, et al. "The Future: Endoscopic Antireflux Repair Via the Endo-Organ Approach". Seminars in Laparoscopic Surgery, Mar. 1995 2:1 66-73.

Gas/Liquid Separation Technology, sulzer Chemtech USA, 8505 E. North Belt St., Humble, Texas 77396, 2009.

Jafri, S., et al. "What is left of the endoscopic antireflux devices?" Current Opinion in Gastroenterology 2009, 25:352-357.

Pace, F., et al. "Review article: endoscopic antireflux procedures—an unfulfilled promise?" Aliment Pharmacol Ther 27: 375-384.2008.

Ruthmann O., et al. "The first Teleautomatic Low-Voltage Prosthesis With Multiple therapeutic Applications: A New Version of the German Artificial Sphincter System". Artificial Organs 34 (8): 635-641. 2010.

Smith, Daniel. "Antireflux Surgery". Surg Clin N Am 88 (2008) 943-958.

Spicak, Julius. "Treatment of Gastroesophageal Reflux Disease: Endoscopic Aspects". Dig Dis 2007 25:183-187.

Torquati, A., et al. "Endoluminal GERD treatments: critical appraisal of current literature with evidence-based medicine instruments". Surg Endosc (2007) 21:697-706.

Vakil, N., et al. "The Montreal Definition and Clkassification of Gastroesophageal Reflux Disease: A Global Evidence-Based Consensus". Am J Gastroenterol 2006 101:1900-1920.

\* cited by examiner

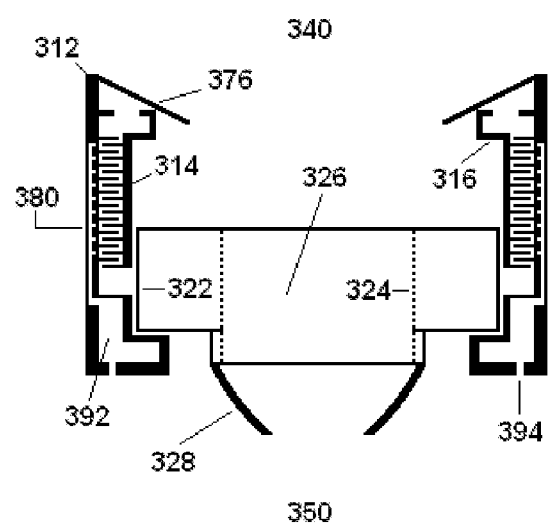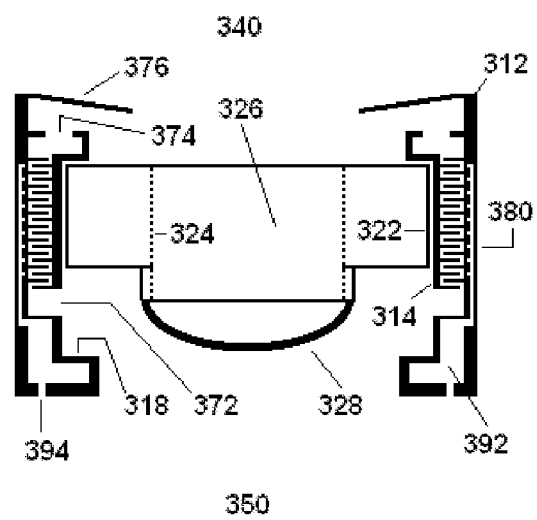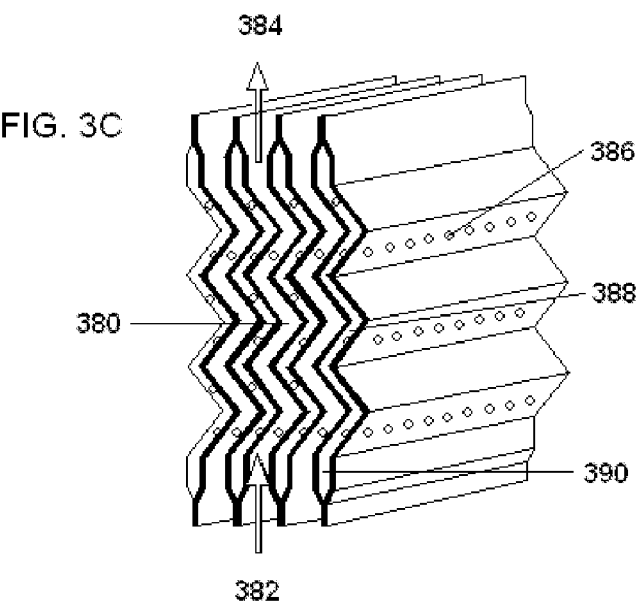

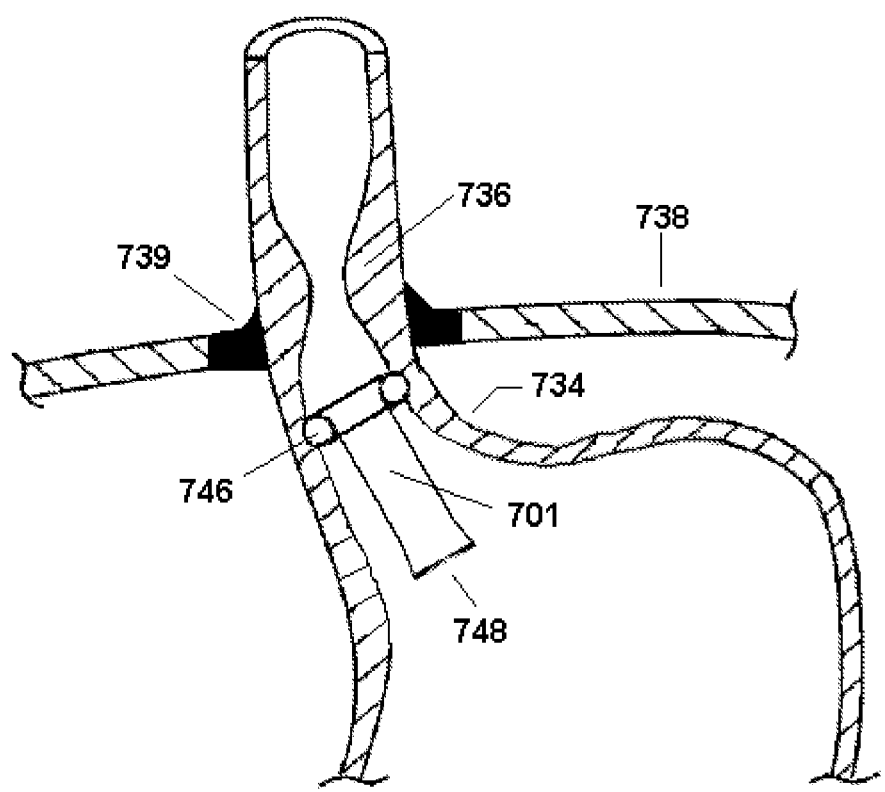

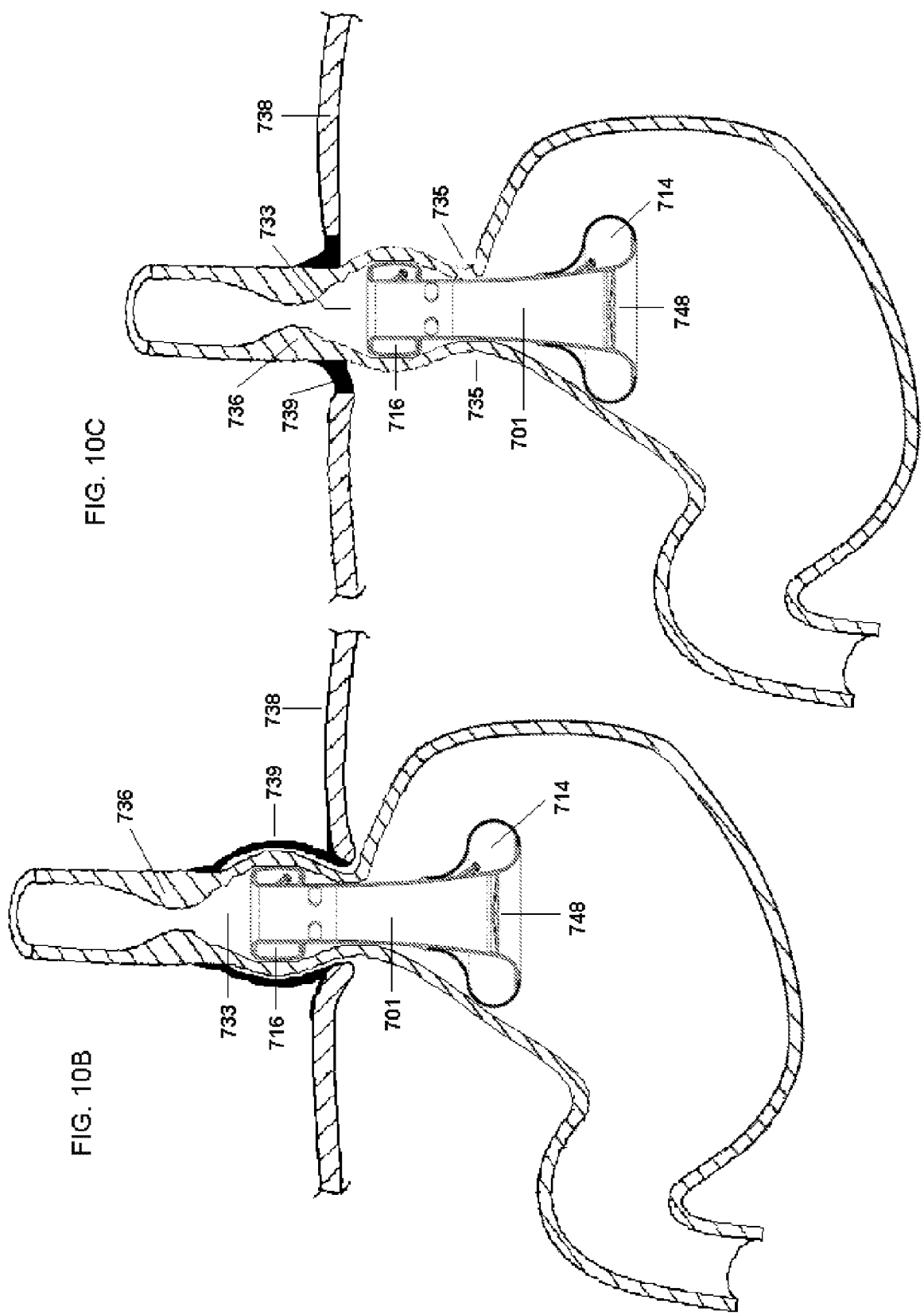

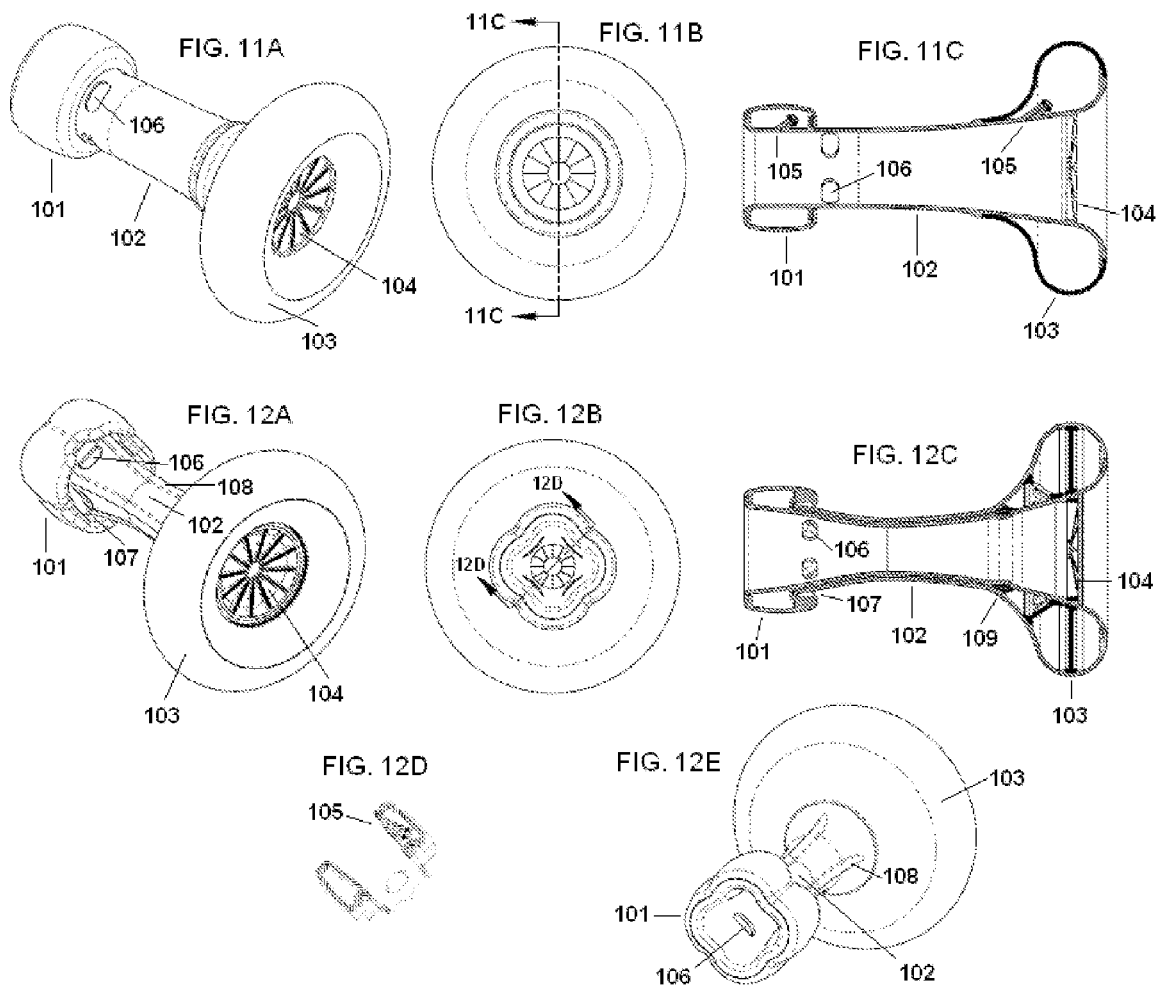

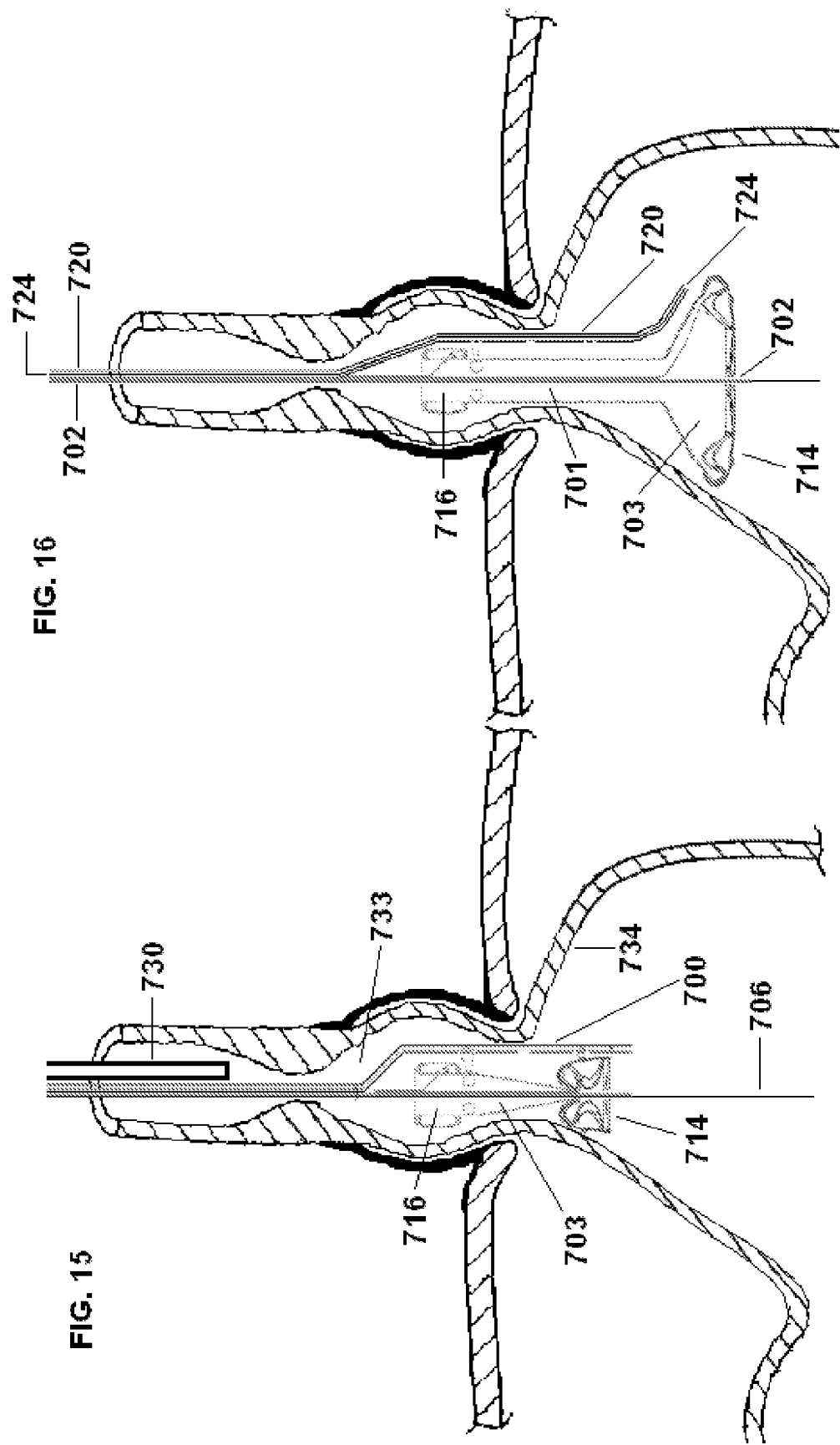

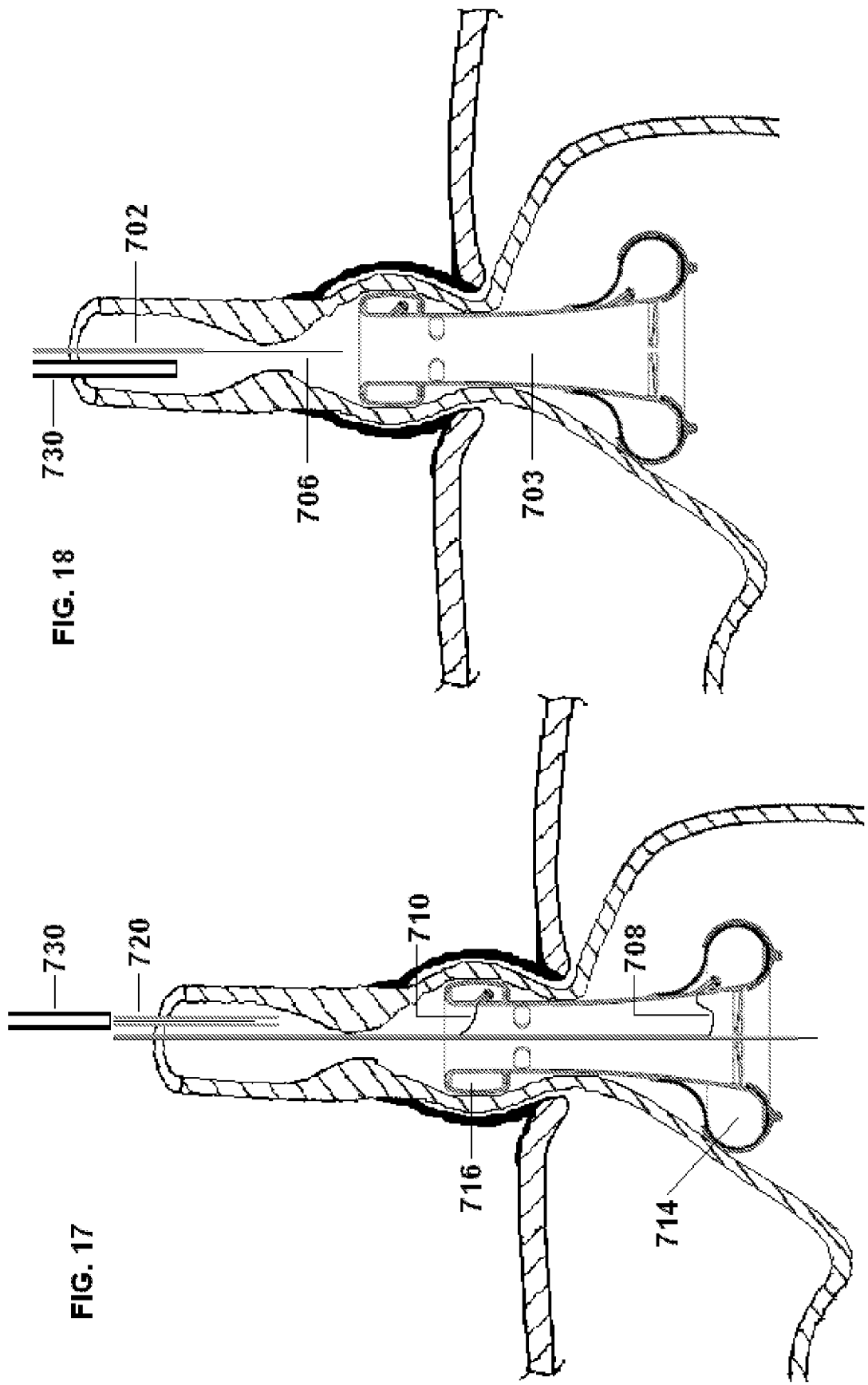

ANTI-REFLUX DEVICES AND METHODS FOR TREATING GASTRO-ESOPHAGEAL REFLUX DISEASE (GERD)

CROSS-REFERENCES TO RELATED APPLICATIONS

This application is a divisional application of co-pending U.S. patent application Ser. No. 12/900,569 filed Nov. 20, 2009. This application is related to commonly assigned co-pending U.S. patent application Ser. No. 12/702,469 filed Feb. 9, 2010, U.S. patent application Ser. No. 12/622,575 filed Nov. 20, 2009, U.S. patent application Ser. No. 12/622,532 filed Nov. 20, 2009, U.S. patent application Ser. No. 12/702,449 filed Feb. 9, 2010, U.S. patent application Ser. No. 12/702,438 filed Feb. 9, 2010 and U.S. patent application Ser. No. 12/702,422 filed Feb. 9, 2010 and U.S. patent application Ser. No. 12/702,411 filed Feb. 9, 2010 and U.S. patent application Ser. No. 12/836,862 filed Jul. 15, 2010; the complete disclosures of which are incorporated herein by reference for all purposes.

BACKGROUND OF THE INVENTION

The field of the present invention relates to methods and devices for the treatment of gastro-esophageal reflux disease (abbreviated as GERD, also abbreviated as GORD for the British spelling gastro-oesophageal reflux disease).

GERD is a disease in which there is reflux (back-flow) of acidic fluid, pepsin, and other injurious substances from the stomach to the esophagus. Initially, the reflux does not erode the esophagus, and the patient is said to have non-erosive reflux disease (NERD). However, when it occurs frequently and over an extended period of time, the reflux damages the mucosal lining of the esophagus. Untreated disease may then progress to erosive esophagitis, pre-cancerous Barrett's metaplasia, or adenocarcinoma of the esophagus.

Thus, GERD is a spectrum of diseases, experienced by many patient subgroups that share the common symptom of reflux. Approximately 10-20% of all individuals in the Western world suffer from GERD, defined by at least weekly significant heartburn and/or acid regurgitation events. In the United States the prevalence is 15-20%, while in Asia the prevalence is less than 5%. Nearly half of the affected individuals report experiencing symptoms for more than 10 years. GERD is often co-morbid with, and may aggravate or be aggravated by: abdominal pain, dysphagia, dyspepsia, asthma, cough, hoarseness, angina, gall bladder disease, laryngitis, otitis, sinusitis, chest pain, and anxiety/depression. The prevalence of GERD increases with age.

The most important factor contributing to the onset of GERD is failure of the anti-reflux barrier that separates the stomach from the esophagus, at the gastro-esophageal junction. The anti-reflux barrier contains two major components: the lower esophageal sphincter (LES) and the crural diaphragm. The LES is sometimes referred to as the "intrinsic" LES, to distinguish it from the crural diaphragm that is sometimes referred to as the "extrinsic LES". The (intrinsic) LES is a ring of muscle within the lower end of the esophagus that spends much of its time in a contracted state, essentially closing the esophageal lumen at that location, thereby providing a mechanical barrier between the stomach and esophagus. The LES is best identified functionally with pressure sensors as a high-pressure zone, surrounding the lumen of the esophagus in its terminal 2 to 4 cm, that relaxes reflexively for about 8 seconds upon swallowing. The LES is often, but not always, thickened relative to the esophageal muscle above it.

The part of the stomach that is attached to the esophagus is known as the cardia. The LES and cardia overlap anatomically but are physiologically distinct in that the LES exhibits reflex relaxation. The angle of His is the acute angle between the esophagus and cardia at the entrance to the stomach. The magnitude of this angle affects the ease with which the contents of the esophagus may pass into the stomach, and vice versa, known as a "flap-valve" effect.

The diaphragm is a muscle that separates the abdomen from the thorax, best known for its role in the mechanics of breathing. A series of apertures within the diaphragm allow the passage of structures between the thorax and abdomen, and the esophagus passes through one of those apertures. In normal individuals, the right crus of the diaphragm is attached circumferentially to the LES by the phreno-esophageal ligament, and this encircling attachment provides additional mechanical support to the LES. Thus, in normal individuals, contraction of the crural diaphragm muscle is concentric with contraction of the muscle of the LES, so the pressure in the terminal portion of the esophageal lumen that is due to muscular contraction of the LES is superimposed upon that which is due to the contraction of crural diaphragm muscle. The sphincter-like contraction of the crural diaphragm increases during inspiration when there is increased abdominal pressure. That increased abdominal pressure tends to promote reflux, but contraction of the crural diaphragm counteracts that tendency.

However, in individuals that have the most common form of hiatal (or hiatus) hernia, the proximal stomach protrudes (prolapses) through the diaphragm, moving the proximal stomach from its normal position in the abdomen and into the thorax. This also moves the LES upwards from the plane of the diaphragm upwards into the thorax. This type of hernia is known as a sliding hiatal hernia, and it appears to be due to a loss of elasticity of the phreno-esophageal ligament that connects the crural diaphragm to the LES, plus a shortening of the esophagus that occurs even normally due to contraction of the longitudinal esophageal muscles after swallowing. The herniated part of the stomach may slide up and down, into and out of the chest. However, if the hernia is large, it may remain within the chest at all times, it which case it is called a fixed or permanent hiatal hernia.

When a hiatal hernia is present, muscular contraction of the (intrinsic) LES is no longer concentric with contraction of the crural diaphragm. Consequently, if luminal pressure measurements are made from the terminal end of the esophagus to the proximal portion of the stomach, two high pressure zones may be measured in individuals with a sliding hiatal hernia—one pressure zone corresponds to the (intrinsic) LES at the gastro-esophageal junction, and the other pressure zone is located below the herniated sac of stomach where the diaphragm now encircles the proximal stomach. Considering that a hiatal hernia changes the mechanics of the anti-reflux barrier, its presence contributes to the onset of GERD. However, the nature of that contribution has long been controversial, due to the multiplicity of other interacting factors that contribute to GERD, as now described.

When both components of the anti-reflux barrier are functioning normally, the lumen of the lower end of the esophagus ordinarily has a pressure that varies from 15-30 mmHg greater than pressure within the stomach. Variations in the LES pressure over that range occur in conjunction with muscle contractions of structures to which the LES is attached, namely, the part of the esophagus that lies above it and the stomach. When the muscle of the LES relaxes, peristaltic bolus pressure, gravity, and residual tension and elasticity of the LES force ingested food, liquids, and swallowed air from the esophagus into the stomach. When the muscle of the LES subsequently contracts, any food remaining in the LES is squeezed into the stomach, and after closing, the LES once again provides a mechanical barrier between the esophagus and stomach by resisting distension. Pressure is also contributed by the crural diaphragm (extrinsic LES), and that pressure varies as a function of breathing, posture, abdominal pressure, coughing and the like. However, the LES is not a one-way valve, because gasses that form in the stomach subsequent to a meal must be vented through the LES in the form of belches, as indicated below.

The state of contraction of the muscle of the LES, as well as the state of contraction of the muscles of the crural diaphragm, are controlled by nerves to those muscles, as well as by local factors including hormones, drugs, and food chemicals. In normal individuals, the LES relaxes reflexively (and the LES luminal pressure decreases) following swallowing and following the peristalsis of the esophagus that accompanies the passage of food. That relaxation makes possible the passage of food and liquids through the opening of the LES, at a rate that is determined by the instantaneous pressure difference between the LES lumen and stomach.

Three mechanisms leading to reflux are now described—TLESR, stress reflux, and LES hypotension.

Unless progression of GERD has reached erosive esophagitis or Barrett's metaplasia, the resting tension of a patient's LES is ordinarily in the normal range (i.e, normotensive). In the case of a normotensive LES, the problem is usually not one of persistent back-flow of the contents of the stomach to the esophagus. Instead, the predominant mechanism of gastroesophageal reflux is transient lower esophageal sphincter relaxation (TLESR). With TLESR, the LES relaxes spontaneously, briefly, and episodically without prior swallowing or esophageal peristalsis. TLESR is caused by control of LES relaxation by the nerves that provide feedback to modulate the state of relaxation and contraction of LES muscle. The feedback is mediated by the vagus nerve, and is often associated with gastric distension and a delayed emptying of the stomach. The same TLESR feedback loop is responsible for normal belching, but GERD patients have acidic refluxate in addition to belched gas.

Stress reflux is another mechanism for producing reflux, wherein excessive intra-abdominal pressure squeezes the stomach to such an extent that the normal pressure generated by the LES and crural diaphragm is insufficient to prevent back-flow.

The cause of gastro-esophageal reflux in certain other individuals may be due to a LES resting tension that is abnormally low (i.e. LES hypotension). Typically, these individuals have erosive esophagitis, and approximately 70% of them have a hiatal hernia. Thus, for those individuals with a hiatal hernia, the hypotension of the LES is exacerbated by the displacement of the LES relative to the diaphragm, which would have normally provided additional external sphincter-like support. Apparently, in individuals with a hypotensive LES, the acidity of repeated reflux damages the ability of the LES to generate pressure, and the loss of that pressure promotes a vicious cycle whereby the loss of pressure produces more reflux acid to damage the LES. Because the pressure differential between the LES and stomach is relatively low in these individuals, back-flow of the contents of the stomach to the esophagus is more likely to be a constant, rather than a transient problem.

A certain amount of reflux is present even in normal individuals, but it is not sensed because refluxed acid is neutralized by bicarbonate-rich saliva, which is brought to the gastro-esophageal junction by peristaltic movement of the esophagus. Therefore, if peristaltic movement in the esophagus is impaired, failure of the reflux clearance mechanism may cause the patient to sense the reflux, even if the anti-reflux barrier is functioning normally.

The actual sensation of reflux (i.e., heartburn or esophageal pain) is thought to be sensed directly by chemo-receptors in the esophagus, or sensed indirectly as tissue damage via inflammatory mediators. It is estimated that even for individuals with GERD, less than 5% of reflux events (pH<4) are sensed as heartburn. However, in some patients, the sensory mechanisms may be defective because those individuals may sense heartburn even though no reflux is present. Some patients may also be hypersensitive to the refluxed material, exhibiting a lower than normal threshold for esophageal pain and abnormally large and prolonged neurological response to a given reflux stimulus.

In any case, esophageal pain is likely to be modulated by the detailed composition of recently ingested food, for example, because fatty foods are more likely to produce heartburn, and their digestion stimulates production of neurotransmitters, hormones, and peptides that may act on the nervous system. Such neuromodulators would act in concert with less specific stimuli that may also play a role, such as psychological stress and anxiety related to anticipation of heartburn, as well as excess sympathetic and diminished parasympathetic tone in the autonomic nervous system.

The severity of damage associated with reflux also depends on the nature of the material that is refluxed. If the contents of the stomach are excessively acidic, this will exacerbate the effects of any reflux. Such excessive acidity is ordinarily due to the nature of the food in the stomach rather than to hypersecretion of gastric acid by the stomach. The potential exposure to reflux acid is a function of the time that food spends in the stomach, and this is in turn a function of the rate of gastric emptying. There is also a tendency in patients with advanced GERD to reflux material to the esophagus that had been previously refluxed from the intestine to the stomach (douodenogastroesophageal reflux or DGER).

The tissue in the vicinity of the gastro-esophageal junction has mechanisms for counteracting potential damage due to reflux and for healing any residual damage. They include barriers within the esophageal tissue to the diffusion of acid and pepsin. Such barriers are anatomical and do not appreciably involve the secretion of a mucin gel barrier. Other defense mechanisms include buffering to maintain intracellular pH, blood circulation to remove damaging substances, and inflammatory responses. If these defense and repair mechanisms are impaired, progression of GERD may be expected to occur. Any therapy for GERD should have as one of its objectives respite from reflux, giving normal defense and repair mechanisms time to be effective.

The typical patient with GERD has an initial complaint of heartburn, acid regurgitation, or reflux-related chest pain. Effortless regurgitation of acidic fluid, especially after meals and worsened by stooping or a supine posture, is particularly suggestive of GERD. According to an international consensus, patients may then be diagnosed as having GERD based on the typical symptoms alone [Nimish VAKIL, Sander V. van Zanten, Peter Kahrilas, John Dent, Roger Jones, and the Global Consensus Group. The Montreal Definition and Classification of Gastroesophageal Reflux Disease: A Global Evidence-Based Consensus. Am J Gastroenterol 2006; 101: 1900-1920]. The first line of therapy for mild GERD is lifestyle changes (avoidance of alcohol, chocolate, fatty foods, etc.; weight loss; elevation of the head of the bed), over-the-counter antacids and foam barriers such as Gaviscon for short-term relief, H2 antagonists for longer term relief, and chewing gum to promote saliva production. If this first line of therapy is not successful, the patient may undergo a trial one to two month treatment with a proton pump inhibitor (PPI), such as esomeprazole, that would reduce the acidity of the reflux.

Patients who are difficult to treat may then be referred to a gastroenterologist for further evaluation and treatment. Ordinarily, upper gastrointestinal endoscopy will first be performed by the gastroenterologist in order to identify visual signs of erosion in the region of the gastroesophageal junction and to determine whether Barrett's metaplasia is present. Biopsies are ordinarily performed only to confirm the presence of Barrett's metaplasia. If esophagitis is found, the patient may continue treatment with different types or doses of proton pump inhibitors.

If the endoscopy results are negative, esophageal manometry may be performed to evaluate esophageal peristalsis and to confirm sphincter position and activity. For patients having a problem primarily with transient LES relaxation, therapy with the GABA agonist baclofen might be tried. Patients may also undergo 24 hour pH testing on proton-pump-inhibitor therapy, in consideration of possible diagnoses other than GERD, such as achalasia. To determine whether non-acid reflux may play a role in patients with proton-pump-inhibitor-resistant reflux symptoms, chronic unexplained cough, or excessive belching, intraluminal impedance tests may also be performed.

GERD is a chronic condition, and after medication for its treatment is stopped, the GERD symptoms will return within a few months in most patients. Some patients therefore prefer a potentially permanent surgical treatment for GERD in lieu of a lifetime of medication. Surgery may also be indicated for the subset of patients for which GERD medications are ineffective, or for patients who cannot tolerate use of those medications because of their association with enteric infections, interference with calcium metabolism, or other side effects. Surgery may also be indicated for patients who have persistent problems associated with regurgitation, notwithstanding successful pharmaceutical treatment of heartburn.

The rationale for a surgical treatment for GERD is that the surgery corrects anatomical defects that are associated with GERD—by moving a hiatal hernia back into the stomach, closing the hiatus of the diaphragm, and strengthening the tissue so as to prevent reoccurrence of a hiatal hernia. The most common such surgery is known as a 360 degree Nissen fundoplication, in which the upper part of the stomach is wrapped (plicated) around the lower end of the esophagus and stitched in place. The surgery may now be performed laparoscopically [C. Daniel SMITH. Antireflux Surgery. Surg Clin N Am 88 (2008) 943-958].

However, disadvantages of fundoplication surgery include the cost of the surgery, plus risks and complications that are associated with surgery in general, such as infection and reaction to anesthesia. Complications can also occur after anti-reflux surgery, and many patients over time will continue to require anti-reflux medications. Such complications include "gas bloat syndrome", dysphagia (pain with swallowing and persistent feeling that something is stuck in the esophagus), dumping syndrome, excessive scarring, and rarely, achalasia. The fundoplication can also come undone over time in about 5-10% of cases, leading to recurrence of symptoms.

There are also special types of fundoplication surgery, but their use is generally limited to patients with special conditions [Derick J. CHRISTIAN, Jo Buyske. Current Status of Antireflux Surgery. Surg Clin N Am 85 (2005) 931-947]. Another type of anti-reflux surgery inserts a C-shaped toroidal ring of silicon around the outside of the esophagus and stomach, at the gastro-oesophageal junction (the Angelchik prosthesis). Although some 25,000 Angelchik prostheses have been inserted worldwide, its use has been discontinued due to problems including dysphagia and migration of the device with erosion attributable to the prosthesis. Nevertheless, such devices are still under development [U.S. Pat. No. 4,271,827, entitled Method for prevention of gastro esophageal reflux, to ANGELCHIK; Patent publication US20060276812, entitled Dynamic reinforcement of the lower esophageal sphincter, to HILL et al.; US20100076573, entitled Methods and apparatus for treating body tissue sphincters and the like, to KUGLER et al]. Another type of surgery, intraluminal valvuloplasty, is based on the premise that augmentation of the acute Angle of His and increasing the length of the esophagus will prevent GERD. [Charles J. FILIPI, Kenan M. Ulualp, et al. The Future: Endoscopic antireflux repair via the endo-organ approach. Seminars in Laparoscopic Surgery 2 (Number 1, 1995): 66-73; J AW BINGHAM. Evolution and early results of constructing an anti-reflux valve in the stomach. Proc. Roy. Soc. Med. 67 (1974):4-8; Patent publications US20040243223 and US20080228285, entitled Transoral endoscopic gastroesophageal flap valve restoration device, assembly, system and method, to KRAEMER et al.; and US20100049221, entitled Tissue fixation devices and assemblies for deploying the same, to BAKER et al.]. However, although such special surgical methods have been known for many years, problems associated with their use have prevented their widespread adoption.

Electrically-controlled prosthetic devices that replace a failed natural sphincter are also under investigation [Patent publication No. US20090259315, entitled Electroactive polymer based artificial sphincters and artificial muscle patches, to BANIK; US20090259093, entitled Artificial sphincter with piezoelectric actuator, to BHAT et al.; Olaf RUTHMANN, Sabine Richter, et al., The first teleautomatic low-voltage prosthesis with multiple therapeutic applications: a new version of the German artificial sphincter system. Artificial Organs 34 (8):635-641 (2010)]. However, these methods are too new to assess the likelihood of their utility.

Endoscopic techniques for the treatment of GERD have been developed as alternatives to medication or surgery. These techniques include the delivery of radiofrequency energy to the gastrooesophageal junction (Stretta), injection of bulking agents (Eneryx), implantation of a bioprosthesis (Gatekeeper) into the LES, and suture plication of the proximal gastric folds (Endocinch, Endoscopic Plication System). Each of these endoscopic techniques may decrease reflux symptoms, improve quality of life, and decrease the need for anti-secretory medications. However, after performing such endoscopic treatments, LES pressure rarely increases, pH normalizes in only 30% of patients, and even mild esophagitis heals infrequently. Furthermore, most insurance does not cover the cost of endoscopic anti-reflux procedures for the treatment or management of gastroesophageal reflux disease (GERD) because they are still considered experimental, investigational or unproven [D. CHEN, C. Barber, P. McLoughlin, P. Thavaneswaran, G. G. Jamieson and G. J. Maddern. Systematic review of endoscopic treatments for gastro-oesophageal reflux disease. British Journal of Surgery 2009; 96: 128-136; Julius SPICAK. Treatment of Gastroesophageal Reflux Disease: Endoscopic Aspects. Digestive Diseases 2007; 25:183-187; Alfonso TORQUATI, William O. Richards. Endoluminal GERD treatments: critical appraisal of current literature with evidence-based medicine instruments. Surg Endosc (2007) 21: 697-706. Gary W. FALK, M. Brian Fennerty, and Richard I. Rothstein. AGA Institute medical position statement on the use of endoscopic therapy for gastroesophageal reflux disease. Gastroenterology 2006; 131:1313-1314; Syed-Mohammed JAFRIA, Gaurav Aroraa, and George Triadafilopoulos. What is left of the endoscopic antireflux devices? Current Opinion in Gastroenterology 2009, 25:352-357; F. PACE, G. Costamagna, R. Penagini, A. Repici, and V. Annese. Review article: endoscopic antireflux procedures—an unfulfilled promise? Aliment Pharmacol Ther 27, 375-384 (2008)].

Although currently available endoscopic methods have had only limited success, the option to have some other form of endoscopic treatment would nevertheless be attractive to patients with GERD who have not been successfully treated with medication, but who are not suitable candidates for surgical treatment. It is therefore an objective of the present invention to provide an improved endoscopic treatment for patients with GERD. In particular, it is an objective of the present invention to provide embodiments of improved endoscopically implanted prosthetic valves and valve-retainers that can significantly reduce the symptoms of reflux in GERD patients. It is also an objective of the present invention to provide treatment for different types of patients with GERD. Yet another objective is to present improved methods for implanting such valves and valve retainers.

Current medical tests to evaluate the pathophysiology of a patient with GERD are expensive, must ordinarily be performed one after the other to provide the comprehensive data that are needed to make a proper diagnosis, and may be inconclusive in regards to their recommendation of which alternate therapeutic strategy to follow. The preferable test would monitor the patient continuously for one or more days, because a patient's GERD symptoms may be intermittent. Accordingly, there is need in the art for ambulatory monitoring devices that can measure multiple GERD-related physiological parameters, thereby providing a prompt and more comprehensive evaluation of the causes of a patient's GERD symptoms, as well to suggest the most suitable therapeutic strategy for treating the patient. An objective of one embodiment of the present invention is therefore to provide such an improved monitoring device. In particular, an objective of one embodiment of the invention is to provide a monitoring device that will simulate and evaluate the potential performance of the above-mentioned improved endoscopically implanted prosthetic valves and valve-retainers, before they are implanted permanently.

SUMMARY OF THE INVENTION

The present invention involves devices, systems and methods for the treatment of GERD. Embodiments of the present invention are particularly useful for patients with a hiatal hernia. Other embodiments of the invention are particularly useful for patients with reflux due to transient lower esophageal sphincter relaxations (TLESR).

Anti-reflux valves and retainers for securing them within the lumen of the esophagus, stomach, or a hiatal hernia are disclosed. The retainers contain inflatable balloons, each of which may be enveloped by a flexible shell that is used to secure the balloon to tissue or to position the balloons. In one aspect of the invention, devices with more than one balloon, a low-profile leaf valve, and a sleeve valve are used to treat reflux in patients with a hiatal hernia. One of the balloons is situated within a hiatal hernia, and the other balloon is situated within the lumen of the patient's stomach. The latter balloon contains a leaf valve. The two balloons are connected with the tubing of a sleeve valve. In one embodiment, the sleeve valve has two walls that may be separated by inflation, and the two balloons as well as the sleeve valve may be inflated through a single balloon-inflation valve. In one embodiment, the balloon within the hiatal hernia may contain an indented portion that inflates differently than the non-indented portion of the balloon, and the sleeve-valve may be supported by external ribs. The indents allow passage of food and liquid around the outside of the hiatal balloon, rather than having them coalesce on the top of the balloon.

In another aspect of the invention, a leaf valve may also be configured for its control by constriction of muscle surrounding the lumen of the gastrointestinal tract, through radial compression of the valve's flange.

In another aspect of the invention, bi-directional combination valves are used to treat or diagnose patients with transient lower esophageal sphincter relaxations (TLESR). They pass reflux through a separate channel, in which gas and liquid reflux are separated. The device contains holes or slots in the surface of a baffle, louver, and/or vane to allow liquid to disengage from the gas. Disengaged liquid drains in channels that are separate from channels through which gas flows.

In another aspect of the invention, the bi-directional combination valve contains electrical components that include a source of electrical power, electrical or electronic sensors, an electronic recording device for recording the state of the sensors, logic circuits for controlling mechanical devices within or around the valve, circuits for providing signals to electrodes within or around the valve, and connections between the electrical components. A mechanical actuator can force the closure of the port where reflux enters the channel. Sutures holding the valve within the lumen of the gastrointestinal tract may also be used as electrodes, which may be used to stimulate the gastrointestinal tract to modulate its state of its muscular contraction. Mechanical vibrations may also be directed by the device towards a musculature of the gastrointestinal tract, used to modulate the state of muscular contraction.

In another aspect of the invention, methods are described for treating GERD patients who (1) have no hiatal hernia, (2) have a hiatal hernia that is fixed in place, or (3) have a hiatal hernia that slides above and below the diaphragm. Methods are described for delivering GERD-treatment devices to their target locations within the patient's gastrointestinal tract. In some embodiments, such delivery methods involve the use of a guidewire, a guidewire tube, a suture tube, balloon inflation tubes, and an endoscope.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, forms are shown in the drawings that are presently preferred, it being understood, however, that the invention is not limited by or to the precise data, methodologies, arrangements and instrumentalities shown, but rather only by the claims.

FIG. 3A illustrates another embodiment of an anti-reflux valve according to the present invention, demonstrating operation of the valve when pressure in the esophagus is greater than pressure in the stomach;

FIG. 3B illustrates the anti-reflux valve of FIG. 3A, demonstrating operation of the valve when pressure in the stomach is greater than pressure in the esophagus;

FIG. 3C illustrates a channel connecting entrance and exit ports of a peripheral channel of the anti-reflux valve of FIG. 3A;

FIG. 10A illustrates one step in a method for treating a patient with one or more of the anti-reflux devices of the present invention;

FIG. 10B illustrates another step of the method of FIG. 10A;

FIG. 10C illustrates another step of the method of FIG. 10A;

FIG. 11A is a perspective view of another embodiment of an anti-reflux device according to the present invention;

FIG. 11B is a top view of the anti-reflux device of FIG. 11A;

FIG. 11C is a cross-sectional view along the axis of the anti-reflux device of FIG. 11A;

FIG. 12A is a perspective view of another embodiment of an anti-reflux device according to the present invention;

FIG. 12B is a top view of the anti-reflux device of FIG. 12A;

FIG. 12C is a cross-sectional view along the axis of the anti-reflux device of FIG. 12A;

FIG. 12D illustrates one portion of the anti-reflux device of FIG. 12A;

FIG. 12E is another perspective view of the anti-reflux device of FIG. 12A;

FIG. 15 illustrates another step in the method of FIG. 14;

FIG. 16 illustrates another step in the method of FIG. 14;

FIG. 17 illustrates another step in the method of FIG. 14; and

FIG. 18 illustrates yet another step in the method of FIG. 14.

DETAILED DESCRIPTION OF THE PREFERRED EMBODIMENTS

Figure 1A:
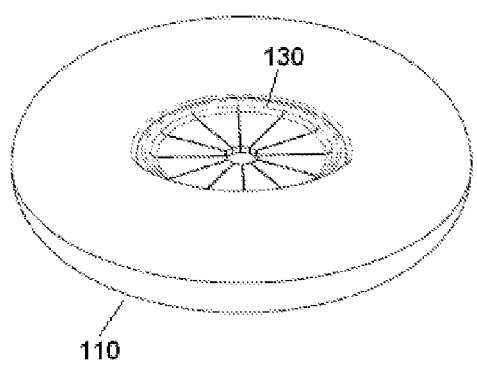
FIG. 1A is a side view of one embodiment of an anti-reflux valve according to the present invention, illustrating a view as seen from the lumen of the esophagus when the anti-reflux valve is in position within the patient.

An objective of the present invention to provide improved endoscopically implanted prosthetic valves and valve-retainers that can significantly reduce the symptoms of reflux in GERD patients. Three types of valves have been previously suggested for the treatment of GERD: unidirectional compact valves, bidirectional compact valves, and collapsible tubing that is sometimes referred to as a sleeve valve. Placement of the proximal end of such valves is typically in a lumen in or near the lower esophageal sphincter (LES) or in a hiatal hernia.

In U.S. Pat. No. 5,314,473, entitled Prosthesis for preventing gastric reflux into the esophagus, to GODIN, a duckbill valve extending from the terminus of the esophagus into a hiatal hernia acts as a one-way valve to prevent reflux. A similar elastomeric valve was described in U.S. Pat. No. 4,265,694, entitled Method of making unitized three leaflet heart valve, to BORETOS et al., but for use in the heart. U.S. Pat. No. 6,264,700, entitled Prosthetic gastro-esophageal valve, to KILCOYNE et al. improves GODIN's design by adding a sleeve for attaching the elastomeric valve to the wall of the esophagus. This design was adapted for the gastro-esophageal junction in Patent applications US20100121461 and US20100121462, entitled Valve, to SOBRINO-SERRANO et al and US20100137998, entitled Esophageal Valve to SOBRINO-SERRANO et al. A similar design was disclosed in U.S. Pat. No. 6,544,291, entitled Sutureless gastroesophageal anti-reflux valve prosthesis and tool for peroral implantation thereof, to TAYLOR, wherein the valve may be implanted without sutures. A similar design using staples was disclosed in U.S. Pat. No. 6,558,429, entitled Perorally insertable gastroesophageal anti-reflux valve prosthesis and tool for implantation thereof, to TAYLOR. U.S. Pat. No. 6,790,237 and U.S. Pat. No. 7,354,455 and applications No. US20050065614 and US20080223476, entitled Medical stent with a valve and related methods of manufacturing, to STINSON, places the one-way valve at the end of a stent. Such unidirectional valves have the disadvantage they do not permit normal reflux (backflow) that accompany belching and regurgitation.

In U.S. Pat. No. 4,846,836, entitled Artificial lower gastrointestinal valve, to REICH, an elastomeric valve permits reflux at high back-pressure by placing two slits in an elastomeric valve that is positioned near the LES: a lower slit opens to permit one-way flow of food and liquid to the stomach, and an upper slit opens at high stomach reverse pressure, to permit one-way reflux only through that upper slit. Patent publication WO2005032422, entitled Gastrointestinal anti-reflux prosthesis apparatus and method, to GODIN, discloses that a single slit can be used in an elastomeric artificial lower gastrointestinal valve, ordinarily acting as a one-way valve to permit passage of food to the stomach, but inverting to provide backflow under high reverse pressure. Patent applications No. US20030191525 and US20040230297, entitled Artificial valve, to THORNTON discloses a similar design. Such an invertible elastomeric two-way valve has long been known in the art [U.S. Pat. No. 4,434,810, entitled Bi-directional pressure relief valve to ATKINSON]. Patent application No. US20100036504 and US20100114327, entitled Valve, to SOBRINO-SERRANO, discloses a similar elastomeric valve that permits flow in two directions, but by using a scaffolding design, inversion of the valve does not occur during backflow. Reflux through pores was also disclosed in US20060058889, entitled Prosthetic valve with pores, to CASE et al.

A channel is defined herein to mean a manufactured conduit for materials that is essentially immobile, even as a valve controlling passage through the conduit opens and closes. It is understood that the length of a channel is ordinarily substantially greater than the diameter of an aperture of a valve for the channel, and that the channel may require valves at either of its ends.

Preferably, in an embodiment of the present invention, retrograde passage of material (reflux) through the device occurs through a channel that does not permit antegrade flow. For example, U.S. Pat. No. 3,159,176, entitled Check-relief valve, to RUSSELL et al., discloses backflow in a valve by opening one immobile channel when reverse pressure is high, but it has not been used for an artificial gastrointestinal valve. None of the above-mentioned gastrointestinal valves contain a channel for separate retrograde (reflux) flow. As an example, in U.S. Pat. No. 4,846,836, entitled Artificial lower gastrointestinal valve, to REICH, an elastomeric valve permits reflux at high back-pressure by placing two slits in an elastomeric valve. Such a two-way valve contains separate antegrade and retrograde valve openings, but those valve openings are not connected to channels, because the openings through which material moves in either direction are not immobile. In fact, proper function of those valves depends upon their distension.

None of the above-mentioned patents or applications disclose, in an artificial gastrointestinal valve, a valve structure with leaves that rotate about a hinge (or more generally flexible attachments that allow valve leaves to flex into a curved profile). Patent publications US20020077696 and US20030212452, entitled Body fluid flow control device, to ZADNO-AZIZI et al., disclose a hinged single-flap valve, but it was used only to prevent backflow. In patent publication US20060064174, entitled Implantable valves and methods of making the same, to ZADNO, leaves that rotate about a hinge are disclosed, but those leaves do not lie in their closed state perpendicular to the axis of the lumen.

Preferably, in embodiments of the present invention, antegrade flow of food and liquid to the stomach is through a low-profile leaf valve. Preferably, when the valve is in its closed position, the leaves of the valve lie essentially in a plane that is perpendicular to the axis of the lumen in which the valve is situated. Preferably, the leaf valve can be configured such that radial compression along its outer circumference (e.g., by tightening of muscle surrounding the lumen of the gastrointestinal tract) can maintain the valve in its closed position, even when pressure gradients, within the lumen in which the valve is situated, would otherwise cause the valve's leaves to bend open at their hinges (or more generally flexible attachments that allow valve leaves to flex into a curved profile).

The simplest form of "tube" or "sleeve" valve consists of a deformable tube that extends the effective length of the esophagus into the stomach, after being sutured at its proximal end to the lumen of the esophagus, gastro-esophageal junction, or hiatal hernia [U.S. Pat. No. 5,861,036, entitled Medical prosthesis for preventing gastric reflux in the esophagus, to GODIN; U.S. Pat. No. 6,764,518 entitled Prosthesis for controlling the direction of flow in a duct of a living organism, to GODIN]. Its function as a valve occurs when it is bent under pressure, changing its geometry to restrict flow. If the tube is sufficiently flexible or floppy, then negative-pressure (effectively, sucking) from within the esophagus or LES will also cause the lumen of the tube to collapse within the stomach, thereby closing the sleeve valve. More generally, if the pressure in the stomach is greater than in the esophagus or LES, such a flexible tube would close. U.S. Pat. No. 6,302,917, entitled Anti-reflux esophageal prosthesis, to DUA et al. and U.S. Pat. No. 7,118,600, US20020032487, US20030060894 and US20070016306, entitled Prosthesis having a sleeve valve, to DUA et al. discloses a device wherein a collapsible sleeve supporting a one-way valve inverts to permit bi-directional flow. U.S. Pat. No. 6,746,489, entitled Prosthesis having a sleeve valve, to DUA et al. discloses a sleeve valve that may invert to provide bi-directional flow. Patent publication No. US20070016306, entitled Gastrointestinal anti-reflux prosthesis apparatus and method, to GODIN, also discloses a bi-directional sleeve valve that inverts to allow for belching or regurgitation. Other such tubular prostheses have collapsible coils embedded in the tube to retard backflow [U.S. Pat. No. 6,887,215, entitled Compressible ureteral stent for comfort, to McWEENEY]. Patent applications No. US20040102855 and US20070112437, entitled Anti-reflux stent, to SHANK disclose a tubular stent that also has a mechanism to prevent backflow.

Preferably, embodiments of the present invention contain sleeve tubing that may act as a sleeve valve. Preferably, embodiments of the present invention comprise a sleeve valve in combination with a unidirectional compact valve or a bidirectional compact valve.

Inflatable implants for a variety of medical purposes were disclosed in U.S. Pat. No. 7,632,291 and application No. US20100076481, both entitled Inflatable implant, to STEPHENS et al. Mention is made in those disclosures of adjusting the pressure within an inflatable implant so as to use it with a collapsible tube, wherein the tube is not permanently affixed to the inflatable implant but simply presses against it to adjust the resting caliber of the tube. However, in preferred embodiments the present invention, an inflatable balloon is permanently affixed to a unidirectional compact valve or a bidirectional compact valve. In other preferred embodiments of the invention, a balloon is used to adjust the flexibility of tubing in a sleeve valve, but the balloon is an integral part of the double-walled sleeve tubing.

For many applications involving the insertion of stents, the stent is expanded by a balloon situated within the stent's lumen. U.S. Pat. No. 7,445,642, entitled Agent eluting stent and catheter, to AMOS et al. discloses the use of an inflated balloon outside a tubular member, in connection with ureteral stents. However, that disclosure is related to the delivery of substances, which is unrelated to the present application.

In patent application US20080133002, entitled Inflatable artificial valve, to GELBART et al. a balloon is inserted into the body and is filled with an elastomeric polymer that sets therein, providing an elastomeric shell structure. However, in preferred embodiments to the present invention, a shell structure is not constructed in situ.

In patent application US20070208429, entitled An Anti Reflux System, to LEAHY, an inflatable balloon is used to position an anti-reflux device, but the bio-degradable balloon is degraded within the stomach after the anti-reflux device is situated within the body of a patient.

In patent application US20100087809, entitled Sphincter treatment apparatus, to EDWARDS et al., energy is delivered to the vicinity of the lower esophageal sphincter for purposes of creating lesions, in which the introduction device comprises a balloon. However, that application is unrelated to the introduction of a prosthetic valve.

Preferably, embodiments of the present invention use one or more inflatable balloons to permanently hold a valve in place within some segment of the esophagus, gastro-esophageal junction, or stomach. Preferably, the balloon is secured on its outside skin by a shell structure. Preferable, the shell structure is sutured, stapled, glued with adhesive, or otherwise attached to the lumen of the patient's esophagus, gastro-esophageal junction, or stomach.

In patent application No. 20100137891, entitled Tissue anchorable devices, to SHALON et al., methods are described for attaching a device to the lumen of the esophagus, stomach, or gastro-esophageal junction, such that a device can move a bit and not be in prolonged contact with any one region of the tissue, which could cause erosion or ulceration. It also discloses sealing methods within the LES, such that gas can escape around the device. Preferably, such methods are used when attaching the device of the present invention to the lumen of the LES.

Figure 1B:
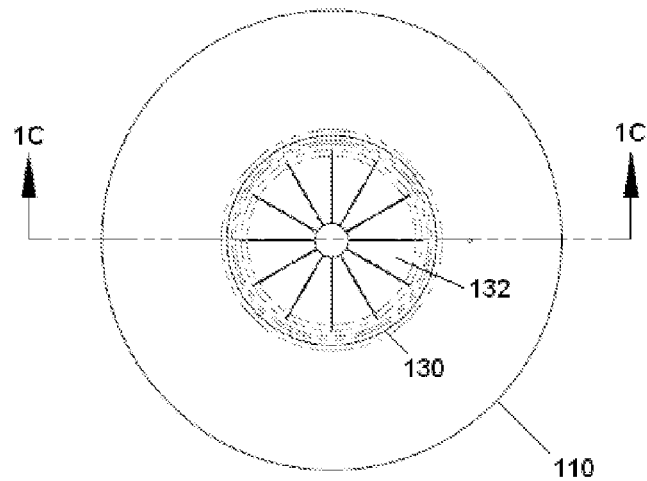
FIG. 1B is a top view of the anti-reflux valve of FIG. 1A as seen from the lumen of the esophagus.
Figure 1C:
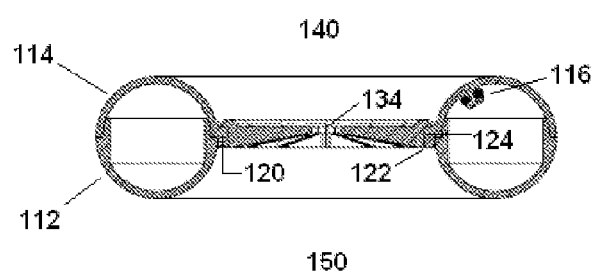
FIG. 1C is a cross-sectional view of the anti-reflux valve of FIG. 1A with the direction of the esophagus shown as the numeral 140.

FIGS. 1A-1C illustrate basic components of the disclosed invention, consisting of a balloon 110 and a valve 130. For purpose of illustration, assume that the device is positioned at the junction between the esophagus and stomach. FIGS. 1A and 1B show the device as seen from the lumen of the esophagus, respectively: from an angle that provides perspective and from a view directly above the device. FIG. 1C shows a cross-section of the device through the section indicated in FIG. 1B, with the direction of the esophagus shown as 140 and the direction of the stomach shown as 150. The valve 130, shown here in its closed position, comprises individual leaves 132. Twelve leaves are shown here, but in general the valve may comprise two or more leaves.

The balloon comprises a balloon skeleton 112, as well as a balloon-to-flange connector 114 that contains the valve's flange 120. The balloon is inflated through its inflation-valve 116. Hinges (or more generally flexible attachments that allow valve leaves to flex into a curved profile) 122 connect the valve leaves to the flange, permitting clockwise rotation of the left leaf seen in FIG. 1C. The flange gives circumferential support to the valve and includes a stop 124. For the left leaf seen in FIG. 1C, the stop blocks counterclockwise rotation of the valve leaf after the valve is closed. Similarly, for the right leaf seen in FIG. 1C, counterclockwise rotation is permitted and clockwise rotation is blocked. A stop-tooth on each leaf also prevents such rotation after the valve is closed.

The center of the valve has a vent-hole 134, which permits substances, particularly gas and regurgitate, to pass through the middle of the valve, irrespective of whether the valve is open or closed. The balloon is not a rigid structure, but may exhibit limited deformation. Therefore, the vent-hole 134 may open somewhat relative to what is shown in FIG. 1B, when there is a high-to-low pressure gradient from the stomach 150 to the esophagus 140, notwithstanding the fact that the valve remains closed under that condition.

Figure 1D:
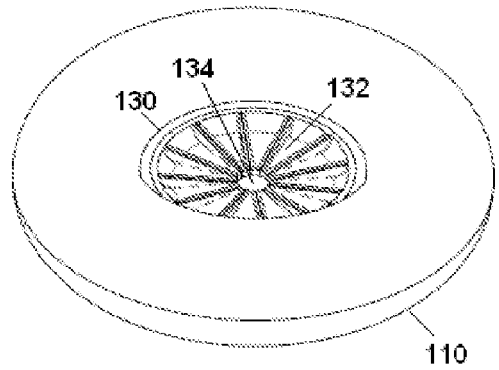
FIG. 1D is a side view of the anti-reflux value of FIG. 1A as seen from the stomach when the valve is in position within the patient.
Figure 1E:
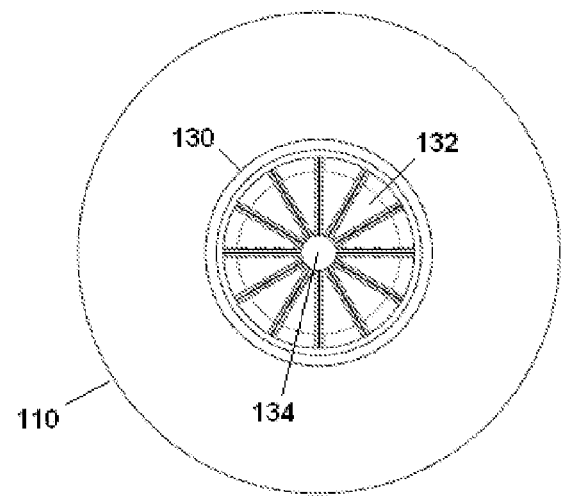
FIG. 1E is a top view of the anti-reflux valve of FIG. 1A as seen from the stomach.

FIGS. 1D, 1E, 1F, and 1G show the balloon 110 and valve 130 from the side opposite of that shown in FIGS. 1A and 1B, i.e., from the stomach. FIGS. 1D and 1E show the device as seen respectively from an angle that provides perspective, and from a view directly above the device. The valve 130, shown in FIGS. 1D and 1E in its closed position, comprises individual leaves 132. As seen there, the leaves are not solid, but have sidewalls that form indentations.

Figure 1F:
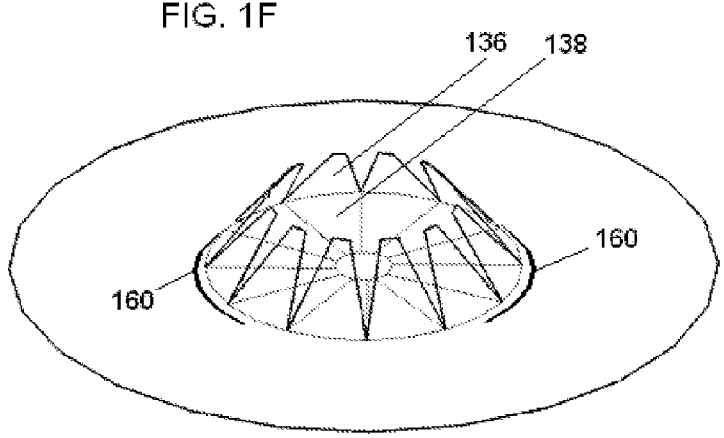
FIG. 1F illustrates the anti-reflux valve of FIG. 1A with optional back-flow slit valves.

As described earlier, when there is a high-to-low pressure differential between the esophagus and stomach, the valve leaves are pushed to rotate about their hinges (or more generally flexible attachments that allow valve leaves to flex into a curved profile), so that the valve opens. FIG. 1F shows the position of a valve leaf when the valve has opened 136, as compared with the position of that leaf when the valve is closed 138. When there is instead a high-to-low pressure differential between the stomach and esophagus, the pressure will force a valve leaf from an open position 136 back to a closed position 138. The valve will also be closed in a zero pressure differential condition.

Figure 1G:
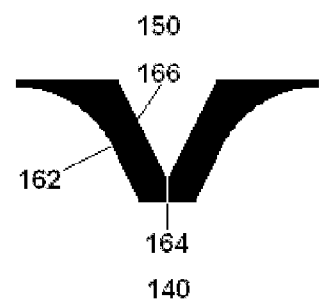
FIG. 1G illustrates the back-flow slit valves of the valve of FIG. 1F.

The vent-hole 134 permits substances, particularly gas and regurgitate, to reflux from the stomach side of the valve to the esophageal side, but for some situations, such as when regurgitation is frequent, it may be advantageous to provide for additional reflux. Accordingly, FIG. 1F also shows the location of optional back-flow relief slit valves 160 that can open when the main valve 130 is closed. The structure of such a slit valve is shown in FIG. 1G, along with its orientation relative to the stomach 150 and the esophagus 140. The slit valve is made of elastomeric material. When the pressure in the esophagus is higher than in the stomach, the pressure on the slit valve's outer sidewalls 162 close any opening in the lumen of the slit 164. But when the pressure in the stomach is higher than the pressure in the esophagus, the inner sidewalls 166 force an opening in the lumen of the slit 164. In the absence of any pressure differential across the slit valve, the valve is constructed to be effectively closed, possibly with only an insignificant open lumen as shown in FIG. 1G.

The valve shown in FIGS. 1A-1C is pressure-actuated, which is to say, the opening or closing of the valve—for either the main valve 130 and for any optional back-flow relief valve 160—is actuated by the direction and magnitude of the pressure difference on the two sides of the valve, i.e., the luminal pressure differential between esophageal and stomach sides. Such a design makes no use of the fact that the lower esophageal sphincter (LES), or other muscle surrounding the lumen of the gastrointestinal tract, may perform similar valve-like functions. In particular, the design makes no use of the normal control of LES contraction and relaxation by the nervous system. For many patients with GERD, the LES still contracts and relaxes, but it is hypotensive, so the LES is no longer able to function as a fully-competent valve. Accordingly, it is preferable that a valve prosthesis be not only pressure-actuated, but that it is also actuated by the contraction or relaxation of the potentially hypotensive LES (or other muscle surrounding the lumen of the gastrointestinal tract). Such a LES-activated prosthetic valve would therefore allow the nervous system to actuate the valve indirectly.

Figure 2A:
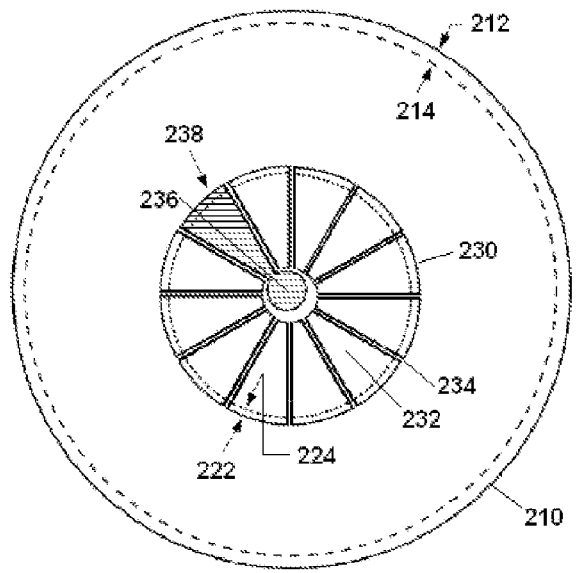
FIG. 2A illustrates an alternative embodiment of an anti-reflux valve without any radial compression according to the present invention.
Figure 2B:
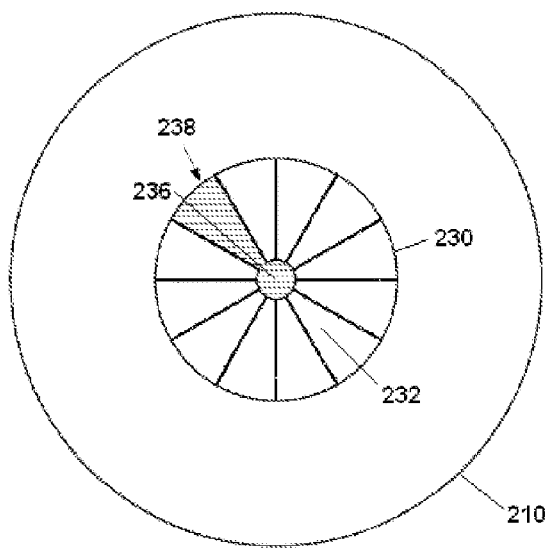
FIG. 2B illustrates the anti-reflux valve of FIG. 1A under radial compression.

Although the valve design shown in FIGS. 1A-1C is not intended for use within the LES, an advantage of the design is that it may be adapted to allow for its radial actuation the LES (or other muscle surrounding the lumen of the gastrointestinal tract), as shown in FIG. 2A. As shown there, the radial compression of the LES is conveyed to the balloon 210 that resides in the lumen of the LES. The balloon in turn conveys that radial compression to the prosthetic valve 230 that is located in the central aperture of the balloon. FIG. 2A shows the balloon and valve when muscle in the LES is relaxed, and FIG. 2B shows the balloon and valve when muscle in the LES contracts. Because the balloon (and any prosthetic shell that surrounds it) is flexible, it will essentially adapt its outer perimeter to the perimeter of the lumen of the LES. Thus, when the LES is relaxed, the outer perimeter of the balloon is shown as 212, and when the LES contracts, the outer perimeter of the balloon is shown as 214. In this embodiment, the flange of the valve is also compressible, so that when the LES is relaxed, the inner perimeter of a valve flange is shown as 222, and when the LES contracts, the inner perimeter of a valve flange is shown as 224.

The embodiment of the valve shown in FIGS. 2A-2B differs from the embodiment of the valve shown in FIG. 1B in two respects. First, when the valve 230 shown in FIGS. 2A-2B experiences no radial compression (i.e., the LES is relaxed, as in FIG. 2A), there is a gap 234 between the individual leaves of the valve 232. When the valve in FIGS. 2A-2B does experience radial compression (i.e., the LES contracts, as in FIG. 2B), that compression forces the leaves of the valve to touch one another, thereby filling any gaps between leaves of the valve.

The second difference between the embodiment of the valve shown in FIGS. 2A-2B, versus the embodiment shown in FIG. 1B, is that the FIGS. 2A-2B embodiment contains a hub 236 that is attached to one of the leaves of the valve 238. When the valve shown in FIGS. 2A-2B experiences no radial compression (i.e., the LES is relaxed, as in FIG. 2A), the gap 234 between the individual leaves of the valve permits those leaves to rotate in response to a pressure difference in one direction across the valve, as shown in FIG. 1F, including rotation of the leaf that is attached to the hub 236. Thus, when the pressure on the esophageal side is greater than the pressure on the stomach side, and the LES is relaxed, the valve will open as before, to permit the passage of food and liquid.

Figure 2C:
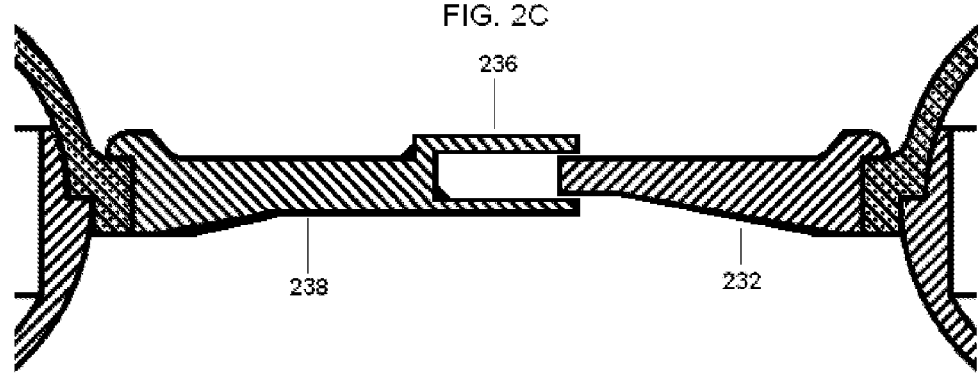
FIG. 2C is a cross-sectional view of one of the leaves of the anti-reflux valve of FIG. 2A.

However, when the valve in FIGS. 2A-2B does experience radial compression (i.e., the LES contracts, as in FIG. 2B), that compression forces the leaves of the valve to press against one another, which in and of itself would resist opening of the valve. Furthermore, the portion of each leaf that is closest to the center of the valve will then enter the hub 236, as shown in FIG. 2C (which is modified from the valve structure shown in FIG. 1C). Referring to FIG. 2C, two valve leaves are shown. The left leaf 238 is attached to the hub 236, and the right leaf 232 lies opposite to it in the valve. When the right leaf 232 enters the hub as in FIG. 2B, rotation of that leaf about its hinge (or more generally flexible attachments that allow valve leaves to flex into a curved profile) is no longer possible, and rotation of the left leaf 238 is also no longer possible.

Therefore, when the LES contracts as shown in FIG. 2B, the leaves and hub collectively resist opening of the valve, even if there is a high-to-low pressure difference from the esophageal to the stomach side of the valve. Thus, the prosthetic valve in FIGS. 2A-2B responds to the state of LES contraction, rather than being solely actuated by luminal pressure.

For many patients suffering from GERD, the lower esophageal sphincter (LES) contracts and relaxes normally, i.e., it is normotensive. For those patients, the GERD may be attributable to reflux during transient LES relaxations (TLESR), rather than to a weak LES. Transient LES relaxations are normal in that they allow stomach gas to be belched in a retrograde direction through the esophagus. However, for reasons that are not always clear, individuals with GERD tend to reflux liquid during such TLESRs, along with the gas.

Accordingly, one would prefer a prosthetic valve that allows retrograde flow through the valve that passes the gas, but does not allow liquid to reflux into the esophagus. U.S. Pat. No. 6,958,079 and application No. US20060041319, entitled Perorally insertable/removable anti-reflux valve, to TAYLOR et al., disclose a gastro-esophageal sleeve valve that closes upon exertion of pressure from the gastric contents, wherein tubing of the sleeve is made of a semi-permeable membrane for passing gas and rejecting liquid. However, use of a semi-permeable membrane to pass refluxed gas and reject liquid when the valve is closed is not a satisfactory solution to the problem, because the membrane (e.g., the GORE-TEX film that was recited) is likely to break under pressure if it is truly a thin film, would offer significant resistance to the passage of gas if it is not truly thin, and is used in practice to separate water vapor and micro-droplets from gas, rather than potentially bulk liquid from gas [e.g., U.S. Pat. No. 7,402,197, entitled Gas/Liquid Separator Including a Liquid Trap Filter, to LARSEN et al.]. Accordingly, the valve should preferably separate gas from liquid in a gas/liquid reflux stream, rather than simply attempt to prevent liquid from entering the reflux stream.

FIGS. 3A-3C discloses a valve structure that actually separates refluxed gas from refluxed liquid and returns the refluxed liquid to its source. The valve may replace the one shown in FIGS. 1A-1C and 2A-2B. Thus, the valve in FIGS. 3A-3C is intended for GERD patients having problems with TLESRs, and the valve shown in FIGS. 1A-1C and 2A-2B may be more appropriate for GERD patients with a hypotensive LES.

For purposes of illustration, the valve shown in FIG. 3A-3C is considered to be positioned in the lumen of the LES. The esophageal side of the valve is indicated as 340, and the stomach side is indicated as 350. FIG. 3A shows operation of the valve when pressure in the esophagus is greater than pressure in the stomach, corresponding to the flow of food and liquid from the esophagus to the stomach. FIG. 3B shows operation of the valve when pressure in the stomach is greater than pressure in the esophagus, corresponding to reflux of material from the stomach to the esophagus.

The valve in FIGS. 3A-3C is designed to normally provide separate routes for antegrade and retrograde flow. Passage of food and liquid from esophagus to stomach occurs in the center of the valve, and passage of refluxate from stomach to esophagus occurs in a channel at the periphery of the valve. Separate valves are used for antegrade and retrograde flow, so the total valve structure shown in FIGS. 3A-3C is called a combination valve. Accordingly, in what follows the valve structure for the central flow is referred to as the central valve, and the valve structure for the peripheral channel is referred to as the peripheral valve.

The peripheral channel is housed in a cylindrical annulus, which has an outer circular surface 312 that is concentric with an inner circular surface 314. The housing for the peripheral channel replaces the valve flange shown in FIGS. 1A-1C and 2A-2B and is attached on its outer circular surface to the balloon shown in those figures. Consequently, the housing of the peripheral channel is fixed in location relative to the lumen of the LES, through its attachment to the balloon. The peripheral channel is located between the inner and outer circular surfaces of the peripheral housing.

The housing for the central valve is also a cylindrical annulus, which has an outer circular surface 322 that is concentric with an inner circular surface 324. The inner surface of the housing defines a lumen 326 through which food and liquid passes from esophagus to the stomach. The outer circular surface of the central housing has a diameter that is slightly smaller than the diameter of the inner circular surface of the housing for the peripheral channel, so that the central housing may be placed within the peripheral housing. The central housing may slide within the peripheral housing, but the range of sliding is limited by an upper stop 316 and a lower stop 318.

The central valve and the peripheral valve each have entrance and exit ports. Food and liquid enter the entrance port of the central housing, passes through the lumen of the central housing 326, and then encounter the actual valve for the central housing 328. The valve is illustrated in FIGS. 3A-3C as an invertible elastomeric dome-shaped valve of the type disclosed in U.S. Pat. No. 4,434,810, entitled Bi-directional pressure relief valve to ATKINSON. However, the valve could have other designs known in the art, such as those disclosed in prior art that is recited herein, or the design shown in FIGS. 1A-1C and 2A-2B.

When the pressure in the esophagus is greater than the pressure of the stomach (shown in FIG. 3A), two things happen to the central housing. First, the pressure causes the central housing to slide to the lower stop 318. Second, under pressure, the central valve 328 opens to allow passage of food and liquid to the stomach.

The peripheral channel also has an entrance port 372 and an exit port 374. As shown in FIG. 3A, when the central housing slides to the lower stop 318, the entrance port 372 for the peripheral channel is blocked, thereby preventing any reflux through the peripheral channel. When the pressure in the esophagus is greater than the pressure of the stomach, the exit port of the peripheral channel is also blocked by hinged flap valves 376, thereby preventing any food and liquid from entering the exit port of the peripheral channel. Those hinged flap valves are forced over the exit port of the peripheral channel by the same pressure gradient that forces food and liquid through the central valve.

The situation is reversed with pressure is greater in the stomach than in the esophagus, as shown in FIG. 3B. Then, two things happen to the central housing. First, the pressure differential causes the central housing to slide to the upper stop 316, thereby opening the entrance port of the peripheral channel 372. Second, the elastomeric central valve 328 is constructed to be normally closed when the pressure is greater at its outer surface than in its lumen (as with the valve shown in FIG. 1G). Therefore, the valve shown in FIG. 3B closes, thereby blocking flow in the central housing.

However, as a safety precaution, the central valve may be selected to be invertible, so that under high back-pressure that may accompany regurgitation, the valve inverts so that reflux through the central housing becomes possible only under that circumstance [U.S. Pat. No. 4,434,810, entitled Bi-directional pressure relief valve to ATKINSON].

With the entrance port of the peripheral channel open, as seen in FIG. 3B, gas and possibly liquid will begin flowing through the peripheral channel, because pressure in the stomach is then greater than the pressure in the esophagus. That pressure will be conveyed to the exit port of the peripheral channel, and as a result, pressure at the exit port of the peripheral channel 374 will force the flap valves 376 into their open position, so as to permit reflux into the esophagus.

The channel connecting the entrance and exit port of the peripheral channel is designed to separate gas from liquid as shown in FIG. 3C. Flow within the channel is from the entrance port side 382 to the exit port side 384. The channel consists of baffles, louvers, and ziz-zag vanes 380 that do little to impede passage of gas, even though the gas must change directions multiple times in moving from the entrance port to exit port. However, momentum forces liquid droplets to impinge on vane surfaces, where they form liquid film that may be drained. Drainage holes and slots 386 in the vane surface allow liquid to disengage from the gas. The disengaged liquid then drains in special channels 388 that are separate from the gas flow. Liquid then collects at the bottom of the drainage channels 390, where it is collected for drainage into a reservoir 392 in FIGS. 3A and 3B). The contents of the reservoir then drain back into the stomach through apertures in the peripheral housing 394. Gas/liquid separators of the type described above are known in the art, as are many other designs that could be considered for this application [Publication entitled Gas/Liquid Separation Technology, Sulzer Chemtech USA, 8505 E. North Belt St., Humble, Tex., 77396].

It is understood that many other embodiments of the valve structure shown in FIGS. 3A-3C could be constructed. Screens can be positioned in at the entrance and exit ports of the peripheral conduit to block particulate matter. The outer conduit could also consist of two separate channels, one of which is as described above and the other is a simple unrestricted channel. Under the high back-pressure of regurgitation, a valve would open the unrestricted channel to allow passage of regurgitated material, and a valve would close to protect the gas/liquid channel from becoming clogged by the regurgitate. If that design is used for the peripheral channel, the invertible central valve could then be replaced by a one-way valve.

It is also understood that the valve structure shown in FIGS. 3A-3C can be adapted for short-term diagnostic use, rather than long-term therapeutic use. In the diagnostic application, it would be used to monitor the frequency and nature of transient LES relaxations, as follows.

It will be noted that during a transient LES relaxation, the central housing is pressed against the upper stop 316, as shown in FIG. 3B. Electrode contacts placed at the site where the central housing touches the upper stop would close an electrical circuit, whenever a transient LES relaxation has occurred and there is sufficient back-pressure to allow reflux.

Furthermore, because the peripheral channel opens after transient LES relaxations, the electrical resistance or impedance between two electrodes placed on opposite sides of the exit port of the peripheral channel can be used to distinguish between the passage of gas and liquid. Thus, when gas passes through the exit port of the peripheral channel, resistance across the exit port is higher than when the exit port is filled with liquid containing electrolytes.

Furthermore, a micro-pH electrode, or other chemical sensor known in the art, can be placed in the exit port or at other positions in the peripheral channel, to distinguish acid from non-acid reflux or other chemical variations.

Furthermore, if flexible springs are mounted parallel to the axis of the peripheral housing, one connecting the upper stop 316 to the top of the central housing, and another spring connecting the lower stop 318 to the bottom of the central housing, tension in those springs may be used as a strain gauges to measure the top-to-bottom pressure differentials that is being experienced by the central housing as that housing moves or rests between the lower stop and upper stop.

Furthermore, if the vanes shown in FIG. 3C are compressed in the radial direction (corresponding to contraction of the LES), electrical capacitance of the vanes will change as a function of the distance between vanes. Accordingly, the capacitance of the vanes may be used as a measurement of radial compression force, taking into account capacitance changes that are also due to the filling with fluid of channels between the vanes. In the alternative, micro pressure sensors may be used to measure radial compression as well as pressure across the lumen, such as the TactArray sensors currently used for high resolution esophageal manometry.

The power source (e.g., battery) and electronics for the above-mentioned electrical sensors, as well as electronics for recording the state of the electrical sensors, may be mounted within the central housing, between its inner and outer diameters. Electrical connection between electronics in the peripheral housing and in the central housing may be made by mounting sliding contacts on the inner surface of the peripheral housing and outer surface of the central housing, parallel to the axis of the peripheral housing. Such contacts would make continuous electrical contact between the peripheral and central housings, despite movement of the housings relative to one another (FIG. 3A versus FIG. 3B).

Such electronic sensors and associated logic circuitry may also be used to control the valve. For example, a linear actuator or piezoelectric actuator may be mounted adjacent to the above-mentioned spring connecting the upper stop 316 to the top of the central housing. If the above-mentioned pH electrode, and/or electrodes distinguishing between the passage of gas and liquid, sense that a liquid acid reflux event is in progress, control circuits within the central housing can cause the linear actuator or piezoelectric actuator to push the central housing from its position in FIG. 3B to its position in FIG. 3A, thereby closing the peripheral channel and terminating the reflux event.

The electronic sensors and associated logic circuitry may also be used to control the valve indirectly, by electrically stimulating contraction of the LES itself to terminate the reflux event [U.S. Pat. No. 6,097,984, entitled System and method of stimulation for treating gastro-esophageal reflux disease, to DOUGLAS; U.S. Pat. No. 7,146,216, entitled Implantable muscle stimulation device for treating gastrointestinal reflux disease, to BUMM; Application No. WO2007/137026, entitled Use of electrical stimulation and neural high frequency stimulation to modulate lower esophageal sphincter pressure, to GEDEON; U.S. Pat. No. 5,716, 385, entitled Crural diaphragm pacemaker and method for treating esophageal reflux disease, to MITTAL et al]. As described below, the valve is situated within a balloon, which is mounted in a shell having suturing-eyes for fixture to the LES (any other desired position within the esophagus or stomach). If the sutures that hold the assembly in place within or near the LES are made of, or impregnated with, electrically conducting material, then the sutures may act as electrodes. If the sutures/electrodes are connected electrically to the electronic sensors and associated logic circuitry within the central housing of the valve, then the valve may electrically stimulate the LES to effect its contraction, so as to terminate a reflux event.

Mechanical vibration of a muscle is also known to affect the state muscular contraction, but to our knowledge, mechanical vibration of the muscle in the lower esophagus, stomach, lower esophageal sphincter has never been suggested as a method for inducing contraction or relaxation of muscles at those anatomical locations. Mechanical vibration has been shown to relax smooth muscle in arteries and in the urethra, but has apparently not been investigated elsewhere. Mechanical vibration has been reported to enhance contraction of striated muscle, with and without simultaneous electrical stimulation. Because the musculature of the lower esophageal sphincter consists primarily of circular smooth muscle, one expects that its mechanical vibration may induce its relaxation, but this has not been demonstrated and the effect of any simultaneous electrical stimulation is likewise unknown. Furthermore, because some investigators did not observe vibrational modulation of such contraction or relaxation, the effect of mechanical vibration on muscle appears to depend on the particular muscle being stimulated, as well as details of the mechanical vibration, such as the vibrational frequency. Furthermore, the effects of mechanical vibration may have an uncertain mechanism, considering that the effect may be on the muscle itself and may also affect the muscle indirectly by stimulating nerves that innervate the muscle.

As regards the vibrational stimulation of nerves that control the contractile state of the muscle of the lower esophageal sphincter, those nerves may be located within the muscle itself or those nerves may lie outside the muscle, but be in close proximity to it. Some of those nerves directly innervate the muscle, and others affect the contractile state of the muscle through reflexes. For example, so-called intramural branches of the vagus nerve pass between muscular layers of the esophagus on their way to the stomach, but the anterior and posterior trunks of the vagus nerve lie outside the lower esophageal sphincter in close proximity to it, because both the esophagus and the vagus nerve pass through the esophageal hiatus of the diaphragm. Compounding the anatomical complexity is the fact that the esophageal plexus of the vagus nerve may branch once in some individuals immediately above the diaphragm, but in other individuals it may branch many times before passing through the diaphragm.

Notwithstanding the uncertainty as to whether mechanical vibration will promote relaxation or contraction of the smooth muscle of the lower esophageal sphincter in any given individual, either eventuality may be of benefit to the patient. If the vibration promotes contraction, then that effect may be used to terminate a transient LES relaxation that is associated with a reflux event. It may also be used to stimulate contraction of a hypotensive LES. If the vibration promotes relaxation, that effect may be used to counteract a hypertensive LES in general, including one that is accompanied by dysphagia and esophageal dysmotility that may be associated with use of the prosthetic valve.

Therefore, in one embodiment of the invention, one or more vibrators are placed in or around the valve or its surrounding balloon. In one embodiment, the vibrators are situated upon the inner or outer skin of the balloon that encloses the device shown in FIGS. 3A-3C, such that the vibrators are in close proximity to the lumen of the LES. In an alternate embodiment, a miniature reciprocating pump is attached to the filling-valve of the balloon, such that the pump causes the balloon's internal pressure to oscillate. The vibrator may be under control of logic circuits described above in connection with the electrical stimulation of the LES using electrodes. The vibration may be performed with or without simultaneous electrical stimulation of the LES. The vibrator may be configured to vibrate mechanical energy in all directions of the lumen of the LES, or it may be configured to vibrate in specific directions, for example in the direction of the anterior or posterior trunk of the vagus nerve. The vibrator may be any vibration-producing device known in the art, including (but not limited to) a linear actuator, an electromagnet, a bimorph, a piezo crystal, an electrostatic actuator, or a speaker coil. In the preferred embodiment, the vibrator produces mechanical vibrations having a frequency of between 1 and 1000 Hz.

Figure 4A:
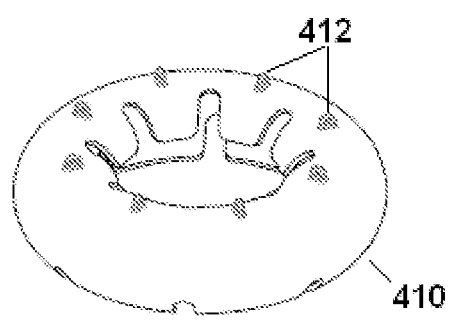
FIG. 4A is a top view of a mounting shell for one of the anti-reflux valves of the present invention.
Figure 4B:
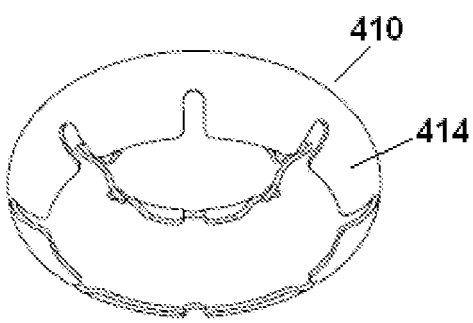
FIG. 4B is a bottom view of the mounting shell of FIG. 4A.

FIGS. 4A-4B show a shell 410, within which a balloon and valve of the present invention are mounted. When positioned in the gastro-esophageal junction, esophagus, or stomach, its lumen will ordinarily be concentric with the lumen that it is intended to fill. The top of the shell, shown in FIG. 4A will ordinarily face towards the esophagus, and the bottom of the shell, shown in FIG. 4B, will ordinarily face towards the stomach.

Suture-eye loops 412 are permanently affixed to the shell, through which suture threading (or other forms of connection) attaches the shell to the tissue that defines the boundary of the target gastro-esophageal, esophageal, or stomach lumen. The suture-eyes are located on the top of the shell, in order that they can be accessible endoscopically. The suture-eye loops 412 may also be used to position the device during its implantation.

Flexible ribs 414 surround the top and bottom apertures of the shell, in order to hold the balloon in place, yet accommodate different inflation sizes of the balloon.

Figure 5A:
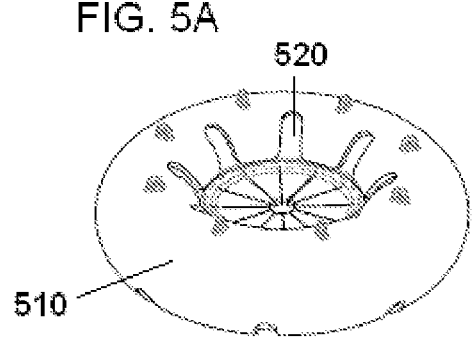
FIG. 5A is a top view of an anti-reflux valve housed within the mounting shell of FIG. 4A.
Figure 5B:
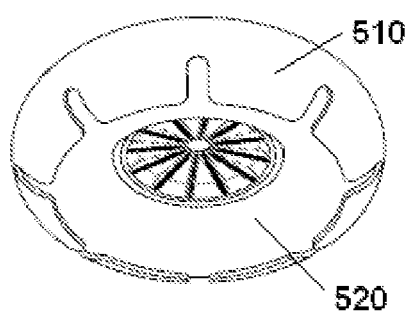
FIG. 5B is a bottom view of the anti-reflux valve and mounting shells of FIG. 5A.

FIGS. 5A-5B shows the device's shell 510 with the balloon and valve placed within the shell. The orientation of FIGS. 5A-5B corresponds to the orientation shown in FIGS. 4A-4C. The top of the shell, shown in FIG. 5A, will ordinarily face towards the esophagus, and the bottom of the shell, shown in FIG. 5B, will ordinarily face towards the stomach. As seen from the top (esophageal) side of the shell in FIG. 5A, the valve flange essentially fills the top aperture of the shell. The inflatable portion of the balloon's skin 520 is seen there only within the shell's inter-rib spaces. The balloon is positioned in such a way that the balloon inflation valve (in FIGS. 1A and 1C) is accessible through one of the inter-rib spaces.

As seen from the bottom (stomach) side of the shell in FIG. 5B, the bottom of the shell has an aperture that is larger in diameter than the aperture through the top of the shell. The larger aperture is needed in order to accommodate insertion of parts of the balloon in its un-inflated state. As described in connection with FIG. 1C, those parts comprise a balloon skeleton, balloon-to-flange connector and balloon skin, as well as the valve's flange and leaves. Some bending of the shell's ribs may be required in order to place the un-inflated balloon within the shell, but as the balloon is inflated, the balloon with attached valve is eventually immobile within the shell. At that point, further inflation of the balloon expands the ribs of the shell.

The shell is made of compressible and distensible material, so that if the shell is placed within the lumen of the lower esophageal sphincter (or other position in the gastrointestinal lumen that is surrounded by musculature), and the LES contracts, then the shell and its enclosed balloon will also be compressed to some extent, as indicated in FIGS. 2A-2B. Use of such compressible and distensible material not only makes possible the radial actuation mechanism shown in FIGS. 2A-2B, but it also makes it possible to reduce the dimensions of the device while it is being inserted endoscopically down the esophagus.

Figure 6A:
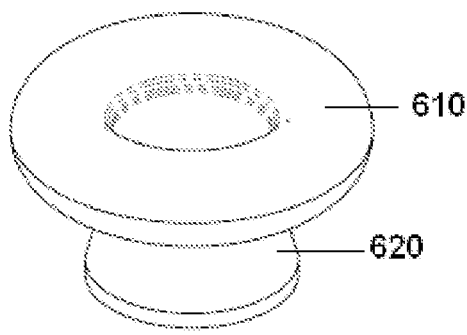
FIG. 6A is a top view of another embodiment of an anti-reflux valve of the present invention incorporating a sleeve.
Figure 6B:
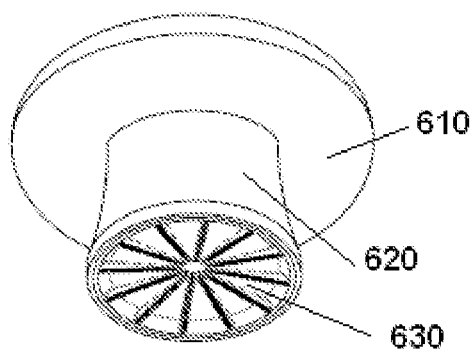
FIG. 6B is a bottom view of the anti-reflux valve of FIG. 6B.

FIGS. 6A-6B demonstrates an alternate embodiment of the invention, wherein the inner flange of the balloon 610 is connected to a sleeve 620 of tubing, instead of to valve leaves. The lumen of the sleeve has a caliber that is typically smaller than the caliber of the inner diameter of the balloon. The orientation of FIGS. 6A-6B corresponds to the orientation shown in FIGS. 4A-4B and 5A-5C. The top of the balloon, shown in FIG. 6A will face towards the esophagus, and the bottom of the balloon with attached sleeve, shown in FIG. 6B, will face towards the stomach. The valve 630 of the device, shown here as the leaf valve of FIGS. 1A-1C, has a flange that is attached to the end of the sleeve.

Although the sleeve shown in FIGS. 6A-6B has a length that is comparable to the inner diameter of the balloon, in practice much longer sleeves will ordinarily be used. This is because it is intended that the sleeve itself, which is constructed from a flexible material, can bend, flatten, and even collapse its lumen, when subjected to external forces or pressures. Accordingly, the sleeve itself can behave as a valve, restricting or preventing flow, depending on the extent to which it is bent over-bent, or flattened by external forces or pressures. Thus, the embodiment of the invention shown in FIGS. 6A-6B is effectively a combination valve, consisting of tubing that may act as a sleeve-valve, plus the leaf valve that is present at the end of the sleeve.

Figure 7A:
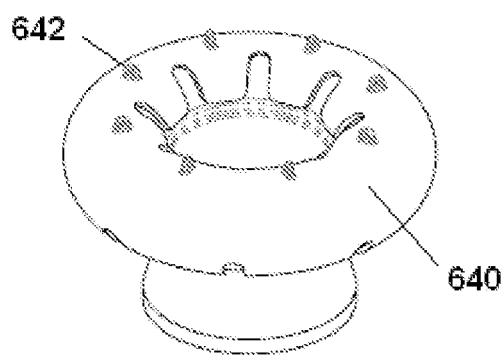
FIG. 7A is a top view of the anti-reflux valve of FIG. 6A within a mounting shell, such as the one illustrated in FIG. 4A.
Figure 7B:
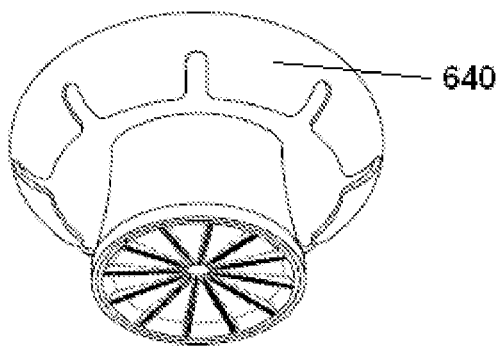
FIG. 7B is a bottom view of the anti-reflux valve and mounting shells of FIG. 7A.

As seen in FIGS. 7A-7B, the embodiment of the invention shown in FIGS. 6A-6B is attached to the lumen of the esophagus, stomach, or lower esophageal sphincter by using the same type of shell 640 that was illustrated in FIGS. 4A-4C and 5A-5B. The orientations of FIGS. 7A and 7B correspond respectively to the orientations shown in FIGS. 6A and 6B. The top of the shell, shown in FIG. 7A will face towards the esophagus, and the bottom of the shell and balloon with attached sleeve and leaf valve, shown in FIG. 7B, will face towards the stomach. The device is attached to the tissue defining the boundary of the lumen of the esophagus, stomach, or lower esophageal sphincter by suturing through the shell's suture-eyes 642.

Figure 8A:
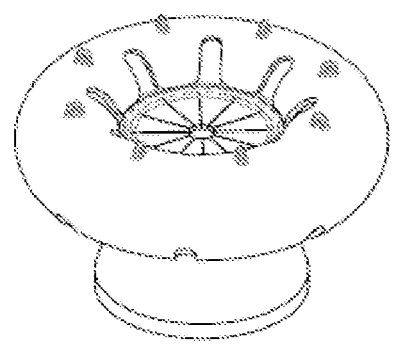
FIG. 8A is a top view of another embodiment of an anti-reflux device according to the present invention.
Figure 8B:
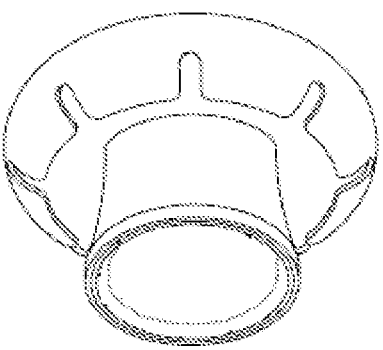
FIG. 8B is a bottom view of the anti-reflux device of FIG. 8A.

In another embodiment of the invention that is shown in FIGS. 8A-8B, the valve shown in FIGS. 6A-6B and 7A-7B is placed in the center of the balloon, as in FIGS. 1A-1C, and sleeve tubing remains attached at the flange of the valve (now in the center of the balloon), while the other end of the sleeve tubing has a lumen that is open, without any valve attached to its distal end. The orientations of FIGS. 8A and 8B correspond respectively to the orientations shown in FIGS. 7A and 7B.

Figure 9A:
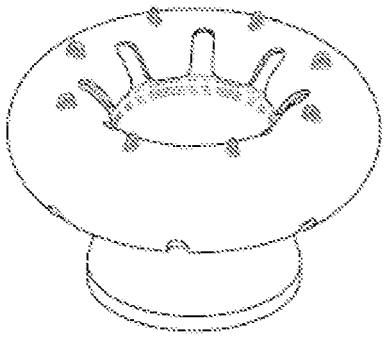
FIG. 9A is a top view of yet another embodiment of an anti-reflux valve according to the present invention.
Figure 9B:
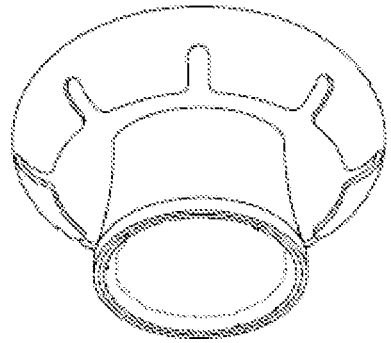
FIG. 9B is a bottom view of the anti-reflux valve of FIG. 9A.

In another embodiment of the invention that is shown in FIGS. 9A-9B, the leaf valve shown in FIGS. 8A-8B is removed, sleeve tubing remains attached at the flange at the inner diameter of the balloon, and the other end of the sleeve tubing has a lumen that is open, without any valve attached to its distal end. In this embodiment, valve function is supplied by the sleeve tube, as described in connection with FIGS. 6A-6B. The orientations of FIGS. 9A and 9B correspond respectively to the orientations shown in FIGS. 7A and 7B.

An exemplary method for treating a patient with the anti-reflux devices described above is shown in FIG. 10A. In this example, the patient with GERD does not have a hiatal hernia. Thus, in FIG. 10A, the diaphragm 738 is attached to the esophagus by the phreno-esophageal ligament 739 in the vicinity of the LES 736. The method of treatment involves advancing a balloon 746 with a valve 748 and/or sleeve 701 directly into the stomach 734 and then fixing the balloon to the stomach tissue around the LES/diaphragm opening to effectively implant a prosthetic valve within the stomach immediately distal to the LES. With the balloon inflated, the lumen of the stomach near the LES is essentially filled by the device. In the alternative, the prosthetic valve and/or sleeve is implanted closer to the LES itself 736 or within the cardia of the stomach more distal to the LES. The implanted device shown in FIG. 10A is of the type shown in FIGS. 6A-6B and 7A-7B, except that the sleeve tubing is longer in FIG. 10A. Fixation of the balloon to the stomach may be made by any convenient method (suture; stapling or the like) possibly using a shell such as the one shown in FIGS. 5A-5B.

As shown in FIGS. 10B and 10C, other embodiments of the device use two balloons instead of one balloon. An intended usage of such two-balloon valves is to treat GERD patients with a hiatal hernia 733. The anatomy shown in FIG. 10B differs from the anatomy shown in FIG. 10A in that the diaphragm 738 is attached to the esophagus by a phreno-esophageal ligament 739 that is deformed to reach the esophagus near the LES 736. One of the balloons in the two-balloon device is part of a so-called "hiatal ring" and is intended to be situated within the lumen of a patient's hiatal hernia. The second of the device's balloons is part of a so-called "gastric ring" and is intended to be situated within a patient's stomach. So, to distinguish between the device's balloons, they are referred to below respectively as the hiatal balloon 716 and the gastric balloon 714. The hiatal balloon is attached to one end of sleeve tubing 701. That sleeve tubing is connected at its other end to the aperture of the gastric balloon.

In FIG. 10B, a patient has a large enough hiatal hernia that the hernia does not slide distally far enough to pass back through the diaphragm opening and back into the stomach. Treatment of this patient involves advancing a balloon with a valve 748 and/or sleeve 701 through the esophagus and into the hiatal hernia with an endoscope and suitable delivery device. A description of a delivery device for this purpose is described below in connection with FIGS. 13-18. Once the balloon is in place, it is inflated and left in the hiatal hernia to operate as a means to retain the device in the GI tract and also allow food to bypass the hernia and go directly from the upper esophagus, through the sleeve, and into the stomach.

In another example that is shown in FIG. 10C, a patient has a sliding hiatal hernia 733 that will slide back into the stomach with some pressure applied, such that the hernia temporarily disappears. This can occur by passing an endoscope through the esophagus and gastro-esophageal junction, then manipulating the endoscope within the stomach to create a downward pressure that causes the hernia to slide back into the stomach. The method of treatment involves placing a balloon with a valve and/or sleeve into the hiatal hernia as in the previous example, except that the balloon is then attached to the stomach tissue within the hernia (suture; stapling or the like). The operator then manipulates the stomach to pull the hernia and the deflated balloon through the diaphragm opening and into the stomach. When the hernia is put back in its normal place, the phreno-esophageal ligament 739 loses much of its prior deformation. The balloon is then inflated to prevent the hernia from sliding back through the diaphragm into the esophagus. This method not only provides an artificial valve; but also potentially cures the patient of the sliding hiatal hernia by fixing the stomach tissue that is susceptible to herniation within the stomach distal to the diaphragm opening. The constrictions shown as 735 are likely to relax once the hernia has been pushed back into the stomach.

As shown in FIGS. 10B and 10C, the aperture of the gastric balloon 714 encircles a valve 748 that is attached to that aperture. In FIGS. 11A-11B and 12A-12B, the valve is shown to be a leaf valve of the type shown in FIGS. 1A-1C, but it could be any type of valve that is known in the art or that is disclosed herein. In contrast, the aperture of the hiatal balloon in FIG. 10B is shown not to encircle such a valve. The orientation of the leaf valve within the aperture of the gastric balloon is such that if pressure is greater in the lumen of the sleeve tubing than in the stomach, then the leaf valve within the aperture of the gastric balloon will open, thereby allowing passage of food and liquid to the stomach. On the other hand, if the pressure is greater in the stomach than in the lumen of the sleeve tubing, then the leaf valve within the aperture of the gastric balloon is oriented so that it will close or remain closed. The valve will also be closed in a zero pressure differential condition.

However, if the sleeve tubing is bent, or even over-bent to collapse the lumen of the sleeve tubing, that will also restrict passage of food and liquid, even if the pressure in the lumen of the hiatal balloon is greater than the pressure in the stomach. Thus, the device shown in FIGS. 10B and 10C has two mechanisms for preventing reflux: the leaf valve and the sleeve tubing acting as a flow restrictor. As described below in connection with a comparison of the embodiments shown in FIGS. 11A-11B and 12A-12B, use of the sleeve tubing as a flow restrictor may be enhanced by using an embodiment that is intended to optimize its restrictor function.

As also shown in FIGS. 10B and 10C, the sleeve tubing contains apertures in its wall that are intended to be positioned where the lower boundary of the hiatal hernia intersects the diaphragm. Those apertures serve three functions. First, they allow the diaphragm to constrict the sleeve tubing at that position, thereby discouraging the hiatal hernia from sliding up and down within the hiatus of the diaphragm. Second, the apertures make that portion of the sleeve tubing the most mechanically weak portion of the tubing, so that when the sleeve tubing bends, it will preferentially bend at that location. Third, the slots also allow drainage of food and liquid from the hiatal hernia to the stomach.

Although the device seen in FIGS. 10B and 10C is not shown as being sutured or otherwise firmly fixed to the wall of the stomach or to the lumen of the hiatal hernia, it may be advantageous to do so. For example, in the sliding hiatal hernia example shown in FIG. 10C, the hiatal balloon may be attached to the stomach tissue within the hernia (suture; stapling or the like). One might also consider attaching the gastric balloon to an upper portion of the stomach wall (e.g., using a shell such as the one shown in FIGS. 4A-4B), in order to construct a "flap valve" having a desired prosthetic Angle of His, in effect substituting for surgical valvuloplasty.

The embodiment of the device shown in use in FIG. 10B is shown in more detail in FIGS. 11A-11C. FIG. 11A shows the device tilted relative to its orientation in FIGS. 10A-10C, so as to reveal the leaves of its leaf-valve. Parts are labeled in FIGS. 11A-11C as follows: hiatal balloon 101, sleeve valve tubing 102, gastric balloon 103, and leaf valve 104. Additional parts include a balloon inflation valve 105 and sleeve-valve apertures 106.

FIG. 11B shows the device as viewed down the orifice of the hiatal balloon, revealing the leaves of the leaf-valve that is situated below within the gastric balloon. FIG. 11C shows the device in cross-section along its axis. By comparing the leaf-valve in that cross section with the leaf-valve in FIG. 1C, it is understood that the leaves of the leaf-valve open in the direction opposite to the direction pointing towards the hiatal balloon.

The device shown in FIGS. 11A-11C is like the device shown in FIGS. 6A-6B, except that it has been modified in the following respects. First, the naked leaf valve seen in FIGS. 6A-6B is surrounded and attached, in the embodiment seen in FIGS. 11A-11C, to a balloon (the gastric balloon) that is similar to the balloon seen in FIGS. 1A-1C. However, unlike the balloon seen in FIGS. 1A-1C, the gastric balloon seen in FIGS. 11A-11C is not symmetrical. As seen in FIG. 11C, it is instead tapered on the side connecting to the sleeve-valve, so as to permit access to a balloon-inflation valve at a narrow angle through the lumen of the sleeve tubing and through the lumen of the hiatal balloon. The tapering also provides mutual mechanical support to the sleeve tubing and gastric balloon, when the sleeve tubing is bent.

Second, whereas the balloon in FIGS. 6A-6B is of the type shown in FIGS. 1A-1C, the corresponding hiatal balloon in FIGS. 11A-11B has a size and shape that is intended to conform to the size and shape of the patient's hiatal hernia. The hiatal balloon has its own balloon-inflation valve, which is lengthened relative to that shown in FIGS. 1A-1C and oriented to permit access at a narrow angle through the lumen of the esophagus. Furthermore, the sleeve tubing in FIGS. 6A-6B differs from that seen in FIGS. 11A-11B, no only because the sleeve tubing in FIGS. 11A-11B is longer than the sleeve tubing in FIGS. 6A-6B, but also because the sleeve tubing in FIGS. 11A-11C contains apertures in proximity to the hiatal balloon. As described above, it is intended that those apertures be positioned where the lower part of the patient's hiatal hernia intersects the diaphragm.

An alternate embodiment of the two-balloon device is shown in FIGS. 12A-12C. FIG. 12A shows the device tilted relative to its orientation in FIGS. 10A-10B, so as to reveal the leaves of its leaf-valve. FIG. 12B shows the device as viewed down the orifice of the hiatal balloon, revealing a partially obstructed view of the leaves of the leaf-valve that is situated below within the gastric balloon. FIG. 12C shows the device in cross-section along its axis. FIG. 12D shows a portion of the device's hiatal balloon in cross-section, including the device's single balloon-inflation valve. FIG. 12E shows the device rotated 180 degrees relative to the orientation shown in FIG. 12A, revealing the apertures within its wall as seen from the lumen.

The device shown in FIGS. 12A-12C modifies the design shown in FIGS. 11A-11C in several respects. First, whereas the sleeve tubing of the device shown in FIGS. 11A-11C has a single wall that is connected on both ends to balloons, the device shown in FIGS. 12A-12C has double-walled sleeve tubing, consisting of an inner (luminal) wall and outer wall. The two walls of the sleeve tubing can be separated by inflating the device through the balloon-inflation valve, via a port in the hiatal balloon. Thus, the inside of the hiatal balloon protrudes into the space between the walls of the sleeve tubing, once the hiatal balloon and sleeve tubing are simultaneously inflated. As the sleeve tubing is inflated, the gastric balloon will also be inflated, through a port connecting the inside of the gastric balloon to the space between walls of the sleeve tubing.

Whereas the hiatal balloon of the device shown in FIGS. 11A-11C expands uniformly from its top to its bottom as it is inflated, this is not the case for the hiatal balloon of the device shown in FIGS. 12A-12C. This is because the part of the hiatal balloon nearest to the inflation port of the sleeve tubing contains an indentation 107 that, upon inflation, can expand radially to a greater extent than the part at the top of the hiatal balloon. The intents allow passage of food and liquid around the outside of the hiatal balloon, rather than having them coalesce on the top of the balloon. In the un-inflated state shown in FIG. 12B, the indented portion of the hiatal balloon constricts the lumen of device, as compared with the device shown in FIG. 11C. The construction of the hiatal balloon in FIGS. 12A-12C is such that the constriction is greatest along two perpendicular axes that lie across the face of the lumen of the device. At 45 degrees angles to those axes, supporting flexible external ribs 108 run the length of the sleeve tubing, from the hiatal balloon to the gastric balloon, terminating near the inflation ports on either end of the sleeve tubing. The gastric balloon also contains an internal supporting flexible skeleton at two locations, which are fenestrated in order to allow for inflation of the gastric balloon.

The non-radially symmetric shape allows food and liquid to drain around the outside of the hiatal balloon, through vents 106, and into the stomach. Furthermore, the design shown in FIG. 12 may seal a hiatal hernia better than the design shown in FIGS. 11A-11C, provided that it is properly inflated, and the design will better immobilize the device within the hiatal hernia. The design shown in FIGS. 12A-12C also allows the device to be inflated through a single balloon-valve.

The lower portion of the hiatal balloon (seen in cross section 12C) is solid in order to maintain the shape of the balloon during peristalsis, preventing the balloon from passing through the hiatus and into the stomach.

The hiatal 101 and gastric 103 balloons are connected via tubes 108, allowing the inflation media to pass between them. During peristalsis the hiatal balloon will be compressed upon by the stomach walls, reducing its volume. This compression will force the inflation media from the hiatal balloon to the gastric balloon, which becomes expanded. As the peristaltic wave passes, compression is removed from the hiatal balloon, the inflation media returns from the gastric balloon to the hiatal balloon, and both balloons return to their pre-compression state. Restricted flow valves can be present in the tubes so as to delay for a specific time the refilling of the hiatal balloon after the peristaltic wave passes. (These valves appear as 109 to the left of the gastric balloon in FIG. 12C). The goal of this feature is to allow the hiatal balloon to conform with the hernia. Otherwise, tissue irritation or erosion may occur.

An exemplary delivery system and method for endoscopically implanting the anti-reflux device similar to the ones shown in FIGS. 10-12 will now be described. The physician first advances an endoscope through the patient's esophagus and into the stomach. A guide wire will then be advanced through the working channel of the endoscope and into the stomach. Preferably, the guide wire is advanced to a position at least 8 inches into the stomach and more preferably greater than 15 inches, coiling upon itself as needed. This ensures that the guide wire will remain in place throughout the implantation process. The endoscope is then removed from the patient and the guide wire left in place.

The anti-reflux device is then attached to a delivery device in preparation for advancing it into position within the patient. In one embodiment, the delivery device comprises a delivery tube having one or more internal lumens. The delivery tube will comprise a material (such as plastic, PTFE, wound metal or the like) having sufficient rigidity to translate a push force from its proximal end to its distal end and sufficient flexibility to allow the distal end of the tube to be endoscopically advanced through the GI tract to a position about 8-15 inches into the stomach. The tube will have a length that extends at least from the distal end of gastric anchor on the anti-reflux device to a position proximal of the hiatal anchor (with the intermediate sleeve valve fully extended). In certain embodiments, the tube may be longer; extending beyond the hiatal anchor and/or long enough to extend through the esophagus and out of the patient's mouth with its distal end within the stomach.

The delivery device further comprises a fastening system for securing the anti-reflux device to the delivery tube such that the two can be advanced together into position within the patient. In one embodiment, the fastening system comprises a series of holes in the delivery tube for receiving a length of thin, flexible material, such as filament, suture, wire, twine, string or the like, therethrough. The suture is attached to the anti-reflux device and the delivery tube through the holes to secure the device to the tube. Preferably, the tube is attached to the distal end of the gastric anchor to ensure that a push force from the proximal end of the tube will translate into a pull force at the distal end of the sleeve to pull the anti-reflux device into position in the gastrointestinal tract. In addition, the tube is preferably attached to the anti-reflux device at another point either at the sleeve valve or proximal to the sleeve valve to ensure that the anti-reflux device remains substantially linear with the delivery tube as the two are advanced through the GI tract. The hiatal anchor may also be attached to the delivery tube. Of course, the anti-reflux device may be secured to the delivery tube at other attachment points as well. For example, it may be advantageous to bundle the gastric anchor into a smaller configuration with suture and then attach the bundled gastric anchor to the delivery tube.

In yet another embodiment, the fastening system comprises a separate suture tube extending along the exterior of the anti-reflux device and the delivery tube. The suture tube will comprise a material (such as plastic, PTFE, wound metal or the like) having sufficient flexibility to allow the distal end of the tube to be endoscopically advanced through the GI tract to a position about 8-15 inches stomach. The tube will have a length that extends at least from the distal end of the gastric anchor on the anti-reflux device to a position proximal of the sleeve valve (with the sleeve fully extended). In certain embodiments, the tube may be longer; extending beyond the hiatal anchor and/or long enough to extend through the esophagus and out of the patient's mouth with its distal end within the stomach. The suture tube may be attached to the delivery tube (e.g., with suture or the like) at points proximal to the hiatal anchor to ensure that the suture tube and delivery tube travel together as the whole system is advanced through the patient's GI tract.

The delivery device preferably further comprises a detaching system for detaching the anti-reflux device from the delivery tube after the anti-reflux device has been advanced into position within the patient. The detaching system is preferably designed such that the device can be detached from the delivery tube by operation outside of the patient. In one embodiment, the detaching system comprises an elongate wire or tube that extends through a lumen within the delivery tube or the suture tube. The elongate wire preferably has a handle at its distal end and a sharp distal edge, cutter or hook on its distal end designed to cut the suture within the suture or delivery tubes. In use, the elongate wire is translated with respect to the delivery or suture tubes (e.g. pulled proximally) such that the sharp distal end cuts each of the sutures passing through the holes in the delivery or suture tubes. Once cut, the sutures are free to pass through the holes such that the anti-reflux device is detached from both the delivery and suture tubes. In another embodiment, the detaching system comprises an elongate wire coupled to one or more rods extending through a lumen within the delivery or suture tube. The rods each have a distal end and a diameter sized to receive a loop of each of the sutures. The elongate wire can be pulled to thereby pull the rods proximally until the loops of suture pass over the distal end of the rods, thereby disengaging the suture loops from the rods so that the suture is free and the anti-reflux device becomes detached from the delivery tube.

In yet another embodiment, the suture tube comprises a series of attachment points for the suture. The attachment points comprise one or more holes for passing a loop of the suture therethrough. A pull wire passes through an internal lumen of the suture tube such that it extends through the loops in each of the sutures. Once the pull wire has been advanced distally through the internal lumen of the suture tube such that each of the suture loops are fastened within the suture tube by the pull wire, the open ends of the sutures are then tied around the delivery tube and the device. This fastens both the delivery tube and the device to the suture tube at each of the attachment points. As the pull wire is pulled proximally, it releases each of the suture loops thereby releasing the device and the delivery tube from the suture tube. In an exemplary embodiment, the attachment points comprise metal spacers having holes therein for receiving the suture loops. Of course, it will be recognized by those skilled in the art that a variety of other devices may be used to suitably detach the device from the delivery tube.

The sleeve valve may be fastened to the delivery tube in its fully elongated state (i.e., approximately 2-10 inches depending on the length of the sleeve tubing). Alternatively, the sleeve may be shortened in an accordion style such that its length from the hiatal anchor to the gastric anchor is less than the fully elongated length. Since the delivery tube is at least semi-rigid and is attached to the gastric anchor and the anti-reflux device at a proximal point, the sleeve will remain in this shortened configuration during advancement of the device through the gastrointestinal tract.

In the preferred embodiment, the anti-reflux device is fastened to the delivery tube such that the delivery tube is adjacent to (or on the side of) the anti-reflux device. Alternatively, the delivery tube may pass through the center of the anti-reflux device (i.e., through the center of the hiatal anchor and/or the gastric anchor and the sleeve valve) and the suture tube will be fastened to the side of the device. In either embodiment, the delivery and/or suture tube(s) will be fastened to the anti-reflux device so as to create a single package that can advance through the gastrointestinal tract of the patient.

Once the anti-reflux device is fastened to the delivery and/or suture tube(s), the proximal end of the guide wire is advanced through a lumen within the delivery tube and then through the endoscope such that the delivery/suture tube(s) and the anti-reflux device are positioned on the guide wire distal to the endoscope. The delivery/suture tube(s) and anti-reflux device are then advanced along the guide wire with the endoscope following the package. The endoscope provides visualization of the advancement of the device and can also be used as a pusher to advance the device along the guide wire. In certain embodiments, the delivery system may further include a separate pusher device designed for placement between the proximal end of the delivery tube and distal end of the endoscope. The pusher may comprise a substantially rigid tube with a distal engagement device designed to engage with the proximal end of the delivery tube and/or the hiatal anchor. For example, the distal engagement device may comprise a cupped shaped member designed to partially house the proximal portion of the hiatal anchor. This provides a solid engagement with the anti-reflux device to more effectively translate a push force to the delivery tube and the device.

The additional push force from the endoscope and/or the pusher device may be necessary if the proximal end of the guide wire withdraws proximally. To inhibit such withdrawal of the guide wire, the system may further include a guide wire with an expandable element (such as a balloon) at its distal end. The expandable element can be expanded within the patient's stomach to prevent the guide wire from withdrawing proximally.

The delivery/suture tube(s) are preferably advanced into the stomach until the gastric anchor has passed into the stomach of the patient. The suture tube is then detached from the anti-reflux device. As discussed above, the suture tube is preferably detached from outside of the patient's body with the detachment system. Thus, the elongate wire or tube is pulled from outside of the body to either cut through the sutures or to free the suture loops such that the sutures disengage from the delivery tube and anti-reflux device. Once the sutures are disengaged from the anti-reflux device, the suture tube may be removed from the patient's body. The hiatal and gastric anchors are then inflated as discussed below and the fill tubes used to inflate the balloons are either cut within the body or pulled such that they automatically detach from the anchors. In one embodiment, the fill tubes pass through a lumen in the delivery tube and through a side hole in the delivery tube proximal to the hiatal anchor. When the fill tubes are pulled from outside of the patient's mouth, the delivery tube creates the necessary counter traction to allow the fill tube to disengage from the hiatal and gastric anchors. This allows the operator to withdraw the fill tubes from outside of the patient. The delivery tube and guide wire may then be removed from the patient.

Figure 13:
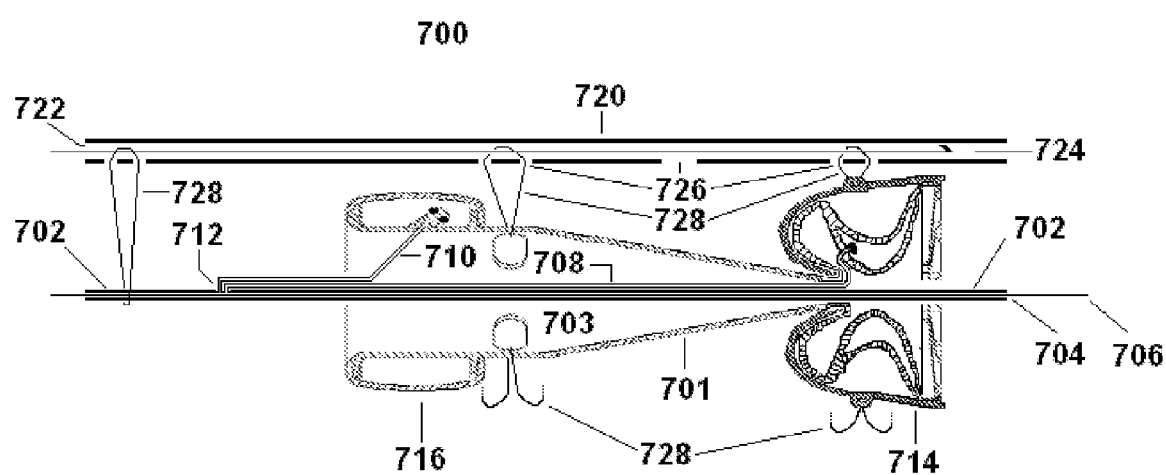
FIG. 13 illustrates one embodiment of a delivery system according to the present invention.

FIG. 13 illustrates one embodiment of a delivery system 700 according to the present invention. As shown, delivery system 700 comprises a guidewire tube 702 configured for passing through an anti-reflux device 703 and having an internal lumen 704 for passage of a guidewire 706 and gastric and hiatal anchor inflation tubes 708, 710. Guidewire tube 702 further comprises an opening 712 to allow inflation tubes 708, 710 to pass out of the internal lumen 704 for coupling to valves in gastric and hiatal anchors 714, 716. Opening 712 is also designed to for the release and removal of the inflation tubes from the gastric and hiatal anchors. As discussed above, pulling on the inflation tubes from outside of the patient will force opening 712 of guidewire tube 702 against the anchors and provide sufficient countertraction for the inflation tubes to disengage from the valves within the gastric and hiatal anchors.

Delivery system 700 further comprises a suture tube 720 having an internal lumen 722 for receiving a pull wire 724 and a series of openings 726 for receiving suture 728. In use, a loop is formed in the suture and then passed through an opening 726. Pull wire 724 is then advanced distally such that it engages the suture loop and retains the suture loop within the lumen 722. The remaining ends of the suture 728 may then be used to tie anti-reflux device 703 to suture tube 720 and guidewire tube 702. In this manner, anti-reflux device 703 may be tied to guidewire tube 702 at a series of points along its length such that the anti-reflux device 703 can be advanced along with the guidewire 706 with guidewire tube 702.

Anti-reflux device 703 is preferably tied such that sleeve 701 is crumpled around guidewire tube 702, and gastric and hiatal anchors 714, 716 are compressed in their uninflated configurations against guidewire tube 702. This facilitates advancement of anti-reflux device 703 through the esophagus and stomach of the patient. In FIG. 13, the gastric anchor is shown with a shell enclosing the gastric balloon (see FIGS. 4A-4B and 5A-5B), such that the shell is bent back around the flange of the valve in a compressed configuration. Suture loops are used to attach the gastric anchor to the suture tube 720, as well as to maintain the gastric anchor in this compact configuration until it is positioned for release into its uncompressed state. Similarly, FIG. 13 shows the sleeve tubing and hiatal balloon in compressed form, although for clarity, wrinkles that would normally accompany their compression were not shown.

When anti-reflux device 703 is in position within the patient, pull wire 724 is pulled distally out of the suture tube 720, thereby disengaging each of the suture loops and releasing anti-reflux device from both suture tube 720 and guidewire tube 702.

Figure 14:
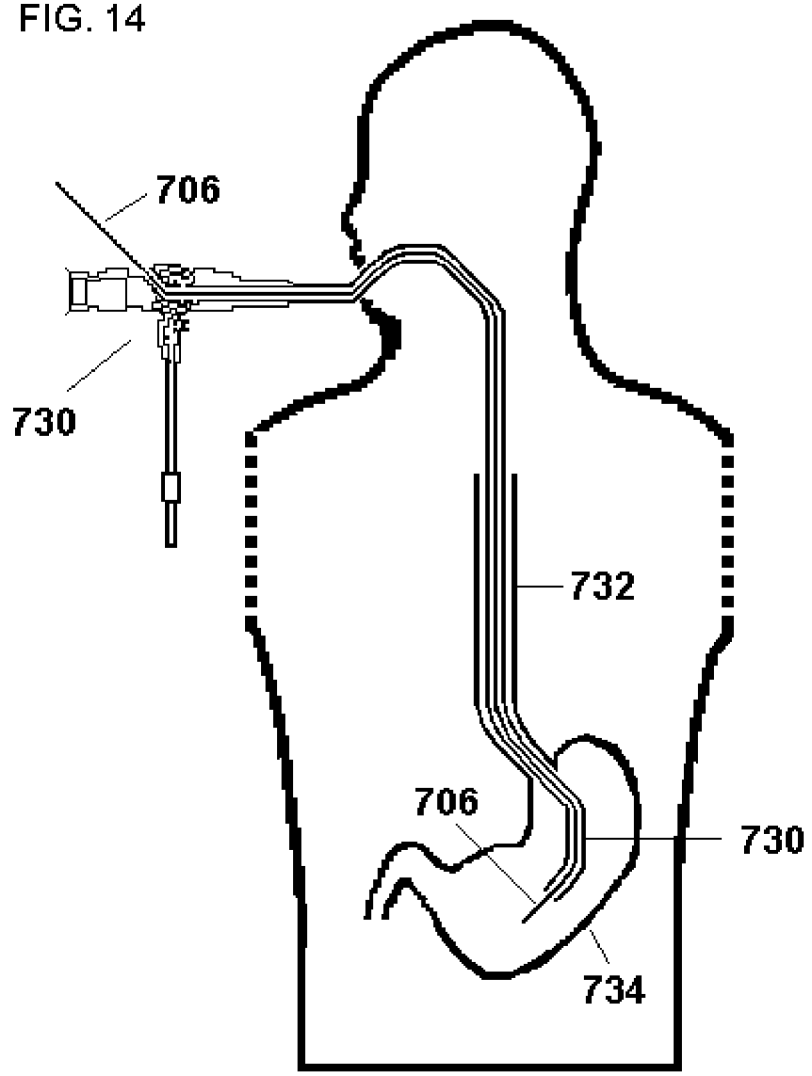
FIG. 14 illustrates one step in a method of implanting an anti-reflux device according to the present invention.

FIGS. 14-18 illustrate one embodiment of a method for implanting an anti-reflux device into the patient. As shown in FIG. 14, the physician first advances an endoscope 730 through the patient's esophagus 732 and stomach 734. A guide wire 706 will then be advanced through the working channel of the endoscope 730 and into the stomach 734. Preferably, the guide wire 706 is advanced to a position at least 8 inches into the stomach and more preferably greater than 15 inches, coiling the guide wire as needed. This ensures that the guide wire will remain in place throughout the implantation process. The endoscope is then removed from the patient and the guide wire left in place.

Referring now to FIG. 15, delivery system 700 and anti-reflux device 703 are then positioned on guide wire 706 as discussed previously, then advanced along guide wire 706 until gastric anchor 714 is positioned within the stomach 734 of the patient and hiatal anchor 716 is positioned within the hiatal hernia 733 of the patient. The physician may advance endoscope 730 to view the device and ensure that it is in the proper position.

Referring now to FIG. 16, the physician may now withdraw pull wire 724 (see FIG. 13) from suture tube 720 to free the tied sutures and disengage anti-reflux device 703 from both suture tube 720 and guide wire tube 702. When this occurs, sleeve 701 will naturally extend and gastric and hiatal anchors 714, 716 will expand into their naturally uninflated configurations.

Referring now to FIG. 17, suture tube 720 may then be removed from the patient. In certain embodiments, the physician may extend a device (such as a snare or the like) through endoscope 730 to assist with the removal of suture tube 720. As also shown in FIG. 17, physician then inflates the anchors 714 and 716 by delivering fluid through inflation tubes 708 and 710. Once the anchors have expanded to the appropriate size (typically about 15-30 ml of fluid), the physician pulls on inflation tubes 708, 710 to disengage them from the valves in the hiatal and gastric anchors. The inflation tubes may then be withdrawn from the patient.

As shown in FIG. 18, the physician then withdraws guide wire tube 702 and guide wire 706 from the patient, and anti-reflux device 703 has been implanted. Endoscope 730 may be used to visualize final placement of the device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A device for treating a patient with gastroesophageal reflux disease and a hiatal hernia, comprising:
   a first anchor movable between a compressed configuration for advancement through an esophagus of the patient into the hiatal hernia and an expanded configuration for residing within the hiatal hernia, the first anchor being inflatable with an inflation fluid;
   a hollow sleeve having proximal and distal end portions; wherein the proximal end portion is coupled to the first anchor and the sleeve is sized and configured to allow material to pass distally from the esophagus at the location of the hiatal hernia through the hollow sleeve and into a stomach of the patient;
   a second anchor coupled to the distal end portion of the sleeve and movable between a compressed configuration for advancement through the esophagus of a patient into the stomach and an expanded configuration for residing within the stomach, the second anchor being inflatable with the inflation fluid;
   a valve structure coupled to said second anchor configured for inhibiting passage of liquids and solids proximally from the stomach of the patient into the esophagus;
   a plurality of hollow tubes integrated within said hollow sleeve and connecting said first anchor and said second anchor to allow transfer of the inflation fluid there between; and
   a two-way valve within each of the hollow tubes configured to allow immediate inflation fluid flow from the first anchor to the second anchor when the hiatal hernia compresses and creates pressure against the first anchor and to delay inflation fluid flow back into said first anchor when the hiatal hernia pressure is removed.

2. The device of claim 1 wherein said valve structure comprises a one-way valve configured to inhibit passage of liquids and solids proximally from the stomach of the patient into the esophagus and configured to allow passage of gases proximally from the stomach to the esophagus.

3. The device of claim 2 wherein the one-way valve is configured to allow passage of liquids, solids and gases distally from the esophagus into the stomach.

4. The device of claim 1 wherein said first anchor comprises an annular membrane expandable to a diameter substantially equal to the diameter of the hiatal hernia.

5. The device of claim 4 wherein the annular membrane defines an internal perimeter having a diameter larger than a diaphragm opening of the patient to inhibit migration of the first anchor through the diaphragm opening into the stomach.

6. The device of claim 1 wherein the second anchor comprises a retainer having an aperture and wherein the valve structure is coupled to a perimeter of the aperture.

7. The device of claim 6 wherein the retainer comprises a flange disposed about an outer perimeter of the valve structure.

8. The device of claim 7 wherein the valve structure comprises one or more leaves hinged at the flange, or leaves configured to flex into a curved profile.

9. The device of claim 6 wherein the retainer defines an outer surface and further comprises loops coupled to the outer surface of the retainer for attachment to the patient's tissue.

\* \* \* \* \*